(12) United States Patent
Vaaje-Kolstad et al.

(10) Patent No.: US 8,377,650 B2
(45) Date of Patent: Feb. 19, 2013

(54) METHOD OF ENHANCING DEGRADATION OF CHITIN

(75) Inventors: Gustav Vaaje-Kolstad, Aas (NO); Vincent G. H. Eijsink, Aas (NO); Svein Jarle Horn, Aas (NO)

(73) Assignee: The Norwegian University of Life Sciences (UMB), Aas (NO)

( * ) Notice: Subject to any disclaimer, the term of this patent is extended or adjusted under 35 U.S.C. 154(b) by 749 days.

(21) Appl. No.: 11/377,611

(22) Filed: Mar. 17, 2006

(65) Prior Publication Data

US 2007/0218046 A1    Sep. 20, 2007

(51) Int. Cl.
    *C12Q 1/34* (2006.01)
(52) U.S. Cl. .......................................................... 435/18
(58) Field of Classification Search .................. None
    See application file for complete search history.

(56) References Cited

U.S. PATENT DOCUMENTS

| | | | |
|---|---|---|---|
| 5,496,934 | A | 3/1996 | Shoseyov et al. |
| 6,399,571 | B1 | 6/2002 | Gray et al. |
| 6,512,166 | B1 | 1/2003 | Harman et al. |
| 6,563,020 | B1 | 5/2003 | Simmons et al. |
| 6,576,427 | B1 | 6/2003 | Kirkpatrick et al. |

FOREIGN PATENT DOCUMENTS

WO         9806859 A1    2/1998

OTHER PUBLICATIONS

Branden et al., "Introduction to Protein Structure Second Edition", Garland Publishing Inc., New York, 1999.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
Vaaje-Kolstad et al. (Crystal Structure and Binding Properties of the *Serratia marcescens* Chitin-binding Protein CBP21, The Journal of Biological Chemistry vol. 280, No. 12, Issue of Mar. 25, pp. 11313-11319).*
Bahrke, Sven, et al., "Sequence Analysis of Chitooligosaccharides by Matrix-Assisted Laser Desorption Ionization Postsource Decay Mass Spectrometry," Biomacromolecules, 3: 696-704 (2002).
Benhamou, Nicole, et al., "Antifungal effect of bean endochitinase on *Rhizoctonia solani*: ultrastructural changes and cytochemical aspects of chitin breakdown," Canadian Journal of Microbiology, 39(3): 318-328 (1993).
Bolar, Jyothi Prakash, et al., "Expression of Endochitinase from *Trichoderma harzianum* in Transgenic Apple Increases Resistance to Apple Scab and Reduces Vigor," Phytopathology, 90(1): 72-77 (2000).
Boraston, Alisdair B., et al., "Carbohydrate-binding modules: fine-tuning polysaccharide recognition," Biochem Journal, 382: 769-781 (2004).
Bourne, Yves, et al., "Glycoside hydrolases and glycosyltransferases: families and functional modules," Current Opinion Structural Biology, 11: 593-600 (2001).
Chu, Hoang Ha, et al., "A *Bacillus amyloliquefaciens* ChbB protein binds β- and α-chitin and has homologues in related strains," Microbiology, 147 (pt 7): 1793-1803 (2001).
Davies, G. J., et al., "Plant Glyco-related Genomics," Biochemical Society Transactions., 30:part 2, 291-297 (2002).
Din, Neena, et al., "C1-Cx revisited: Intramolecular synergism in a cellulase," Proc. Natl. Acad. Sci. USA, 91: 11383-11387 (Nov. 1994).
Din, Neena, et al., "Non-Hydrolytic Disruption of Cellulose Fibres by the Binding Domain of a Bacterial Cellulase," Bio/Technology, 9: 1096-1099 (Nov. 1991).
Ding, Xiongfei, et al., "Insect resistance of transgenic tobacco expressing an insect chitinase gene," Transgenic Research, 7(2): 77-84 (1998).
Folders, Jindra, et al., "Identification of a Chitin-Binding Protein Secreted by *Pseudomonas aeruginosa*," Journal of Bacteriology, 182:5, 1257-1263 (Mar. 2000).
Gao, Pei-Ji, et al., Non-hydrolytic Disruption of Crystalline Structure of Cellulose by Cellulose Binding Domain and Linker Sequence of Cellobiohydrolase I from *Penicillium janthinellum*, Acta Biochimica et Biophysica Sinica, 33:1, 13-18 (2001).
Henrissat, Bernard, et al., "New families in the classification of glycosyl hydrolases based on amino acid sequence similarities," Biochem J., 293: 781-788 (1993).
Herrera-Estrella, Alfredo, et al., "Chitinases in biological control," Chitin and Chitinases, ed. by P. Jolles and R. A.A. Muzzarelli, 171-184 (1999).
Hoell, Ingunn A., et al., "Overexpression and characterization of a novel chitinase from *Trichoderma atroviride* strain P1," Biochemica et Biophysica Acta, 1748: 180-190 (2005).
Hollis, Thomas, et al., "Kinetic Analysis of Barley Chitinase," Archives of Biochemistry and Biophysics, 344:2, 335-342 (Aug. 15, 1997).
Horn, Svein Jarle, et al., "A reliable reducing end assay for chito-oligosaccharides," Carbohydrate Polymers, 56: 35-39 (2004).
Kolbe, Steffi, et al., "The *Streptomyces reticuli* α-chitin-binding protein CHB2 and its gene," Microbiology, 144 (Pt 5): 1291-1297 (1998).
Lorito, Matteo, et al., "Synergistic interaction between fungal cell wall degrading enzymes and different antifungal compounds enhances inhibition of spore germination," Microbiology, 140: 623-629 (1994).
Okamuro, Jack K., et al., "Regulation of Plant Gene Expression: General Principles," The Biochemistry of Plants, 15: 1-82 (1989).
Peter, Martin G., "Chitin and Chitosan from Animal Sources," in Biopolymers, vol. 6: Polysaccharides II, A. Steinbuchel, Ed., Weinheim: Wiley VCH, 2000, pp. 481-574.
Saito, Akihiro, et al., "Characteristics of a *Streptomyces coelicolor* A3(2) Extracellular Protein Targeting Chitin and Chitosan," Applied and Environmental Microbiology, 67:3, 1268-1273 (Mar. 2001).
Schnellmann, Jürgen, et al., "The novel lectin-like protein CHB1 is encoded by a chitin-inducible *Streptomyces olivaceoviridis* gene and binds specifically to crystalline α-chitin of fungi and other organisms," Molecular Microbiology, 13:5, 807-819 (1994).

(Continued)

*Primary Examiner* — Suzanne M Noakes
*Assistant Examiner* — Jae W Lee
(74) *Attorney, Agent, or Firm* — Rothwell, Figg, Ernst & Manbeck, p.c.

(57) ABSTRACT

The present invention provides a method of enhancing chitin degradation or weakening the structure of a chitin substrate comprising exposing chitin to a non-hydrolytic chitin binding protein (CBP). The invention further provides a method of enhancing chitin degradation comprising exposing chitin to a non-hydrolytic CBP and a chitin hydrolase. Compositions, including fungicides, comprising non-hydrolytic CBPs and transgenic plants comprising exogenous nucleic acid molecules encoding a non-hydrolytic CBP are also provided.

18 Claims, 7 Drawing Sheets

OTHER PUBLICATIONS

Figure 1:
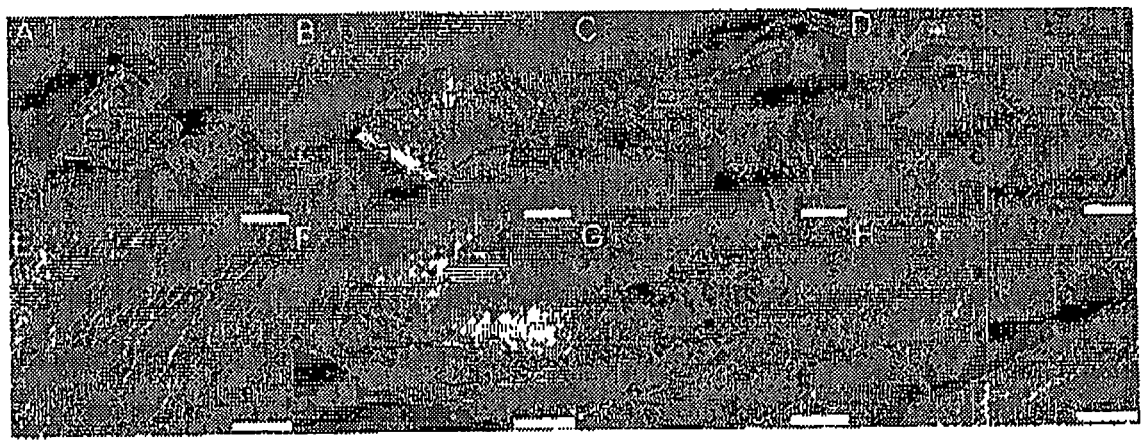

Sunna, Anwar, et al., "A Gene Encoding a Novel Multidomain β-1,4-Mannanase from *Caldibacillus cellulovorans* and Action of the Recombinant Enzyme on Kraft Pulp," Applied and Environmental Microbiology, 66:2, 664-670 (Feb. 2000).

Suzuki, Kazushi, et al., "Chitin Binding Protein (CBP21) in the Culture Supernatant of *Serratia marcescens* 2170," . Biosci. Biotechnol. Biochem., 62:(1), 128-135 (1998).

Svergun, Dmitri I., "Solution Structure and Conformational Changes of the Streptomyces Chitin-Binding Protein (CHB1)," Biochemistry, 39: 10677-10683 (2000).

Tsujibo, Hiroshi, et al., "Identification and Characterization of the Gene Cluster Involved in Chitin Degradation in a Marine Bacteriium, *Alteromonas* sp. Strain 0-7," Applied and Environmental Microbiology, 68:1, 263-270 (2002).

Vaaje-Kolstad, Gustav et al., "Interactions of a Family 18 Chitinase with the Designed Inhibitor HM508 and Its Degradation Product, Chitobiono-δ-lactone," The Journal of Biological Chemistry, 279:5, 3612-3619 (Jan. 30, 2004).

Vaaje-Kolstad, Gustav, et al., "The Non-catalytic Chitin-binding Protein CBP21 from *Serratia marcescens* Is Essential for Chitin Degradation," The Journal of Biological Chemistry, 280:31, 28492-28497 (Aug. 5, 2005).

Zeltins, Andris, et al., "Specific interaction of the *Streptomyces* chitin-binding protein CHB1 with α-chitin The role of individual tryptophan residues," Eur. J. Biochem, 246:2, 557-564 (1997).

Zeltins, Andris, et al., "Visualization of α-Chtin with a Specific Chitin-Binding Protein (CHB1) from *Streptomyces olivaceoviridis*," Analytical Biochemistry: 231:2, 287-294 (1995).

Official Report of Australian Government IP Australia for Australian application No. 2006201124 dated Mar. 23, 2012.

* cited by examiner

METHOD OF ENHANCING DEGRADATION OF CHITIN

BACKGROUND

Chitin is a linear insoluble polymer of β(1-4)-linked N-acetylglucosamine, which is a common consistent of fungal cell walls, shells of crustaceans, and exoskeletons of insects. It is the second most abundant polymer in nature and each year more than one billion tons of chitin is produced in the biosphere, mainly by insects, fungi, crustaceans, and other marine organisms.

In nature, two major types of chitin occur that are the characterized by an anti-parallel (α-chitin) or a parallel (β-chitin) arrangement of the polymer chains.

Despite its resilience, insolubility, and abundant production, chitin does not accumulate in most ecosystems, suggesting that nature has developed efficient processes for chitin degradation. Chitin is degraded for example by chitinases. Chitinase enzymes are found in plants, microorganisms, and animals. Bacterial chitinase helps to provide a carbon source for bacterial growth. Insects produce chitinase to digest their cuticle at each molt. In plants, chitinase is thought to provide a protective role against parasitic fungi.

Chitinases have been cloned from various species of microorganisms and have been categorised into two distinct families, designate family 18 and family 19 of the glycoside hydrolases, based on sequence similarities (Henrissat and Bairoch, Biochem, J. 293: 781-788 (1993)).

In addition to being important for biomass turnover, chitin degradation is essential in a variety of biological processes. For example, plants are known to produce chitinases in response to attack by chitin-containing fungi, whereas some non-pathogenic fungi such as Trichoderma species are considered as "biocontrol" agents because of their ability to inhibit other, chitin-containing fungi. While chitin-containing organisms may be inhibited by exogenous chitinolytic activity, they do need some endogenous chitin turnover as part of morphological and developmental processes. A further example concerns insect viruses, which produce chitinases to disintegrate the peritrophic matrix of their organism, during the first stage of infection thereby increasing virus infectiousness.

Degradation of chitin has a number of important applications. For example, chitinases have been shown to have fungicidal activity, and to ply a role in infectivity of insect viruses. There are also several examples of transgenic plants which by expressing a foreign chitinase gene, have acquired increased resistance towards certain fungal pathogens.

Degradation products of chitin which include the monomeric sugar, N-acetylglucosamine, or oligosaccharides of N-acetylglucosamine can also be used for various different applications.

It can be seen that chitin degradation is important in a number of different fields. Although chitinase enzymes have been known for some time and have been studied in various systems, methods of improving the efficiency or the rate of degradation of chitin would be desirable. The inventors' finding that the efficiency of chitin degradation can be influenced by a chitin binding protein provides a means by which the efficiency of chitin degradation can be modulated artificially, by exposing chitin to such proteins.

In work leading up to the present invention, it has surprisingly been shown that efficient chitin degradation by chitinases in the Gram negative soil bacterium Serratia depends not only on the three Serratia chitinases, by also on the action of a small non-catalytic protein, CBP21, which binds to the insoluble crystalline chitin substrate on which its effect was tested. Although not wishing to be bound by theory, the binding of this non-catalytic protein is believed to lead to structural changes in the chitin substrate, which result in increased substrate accessibility for the chitinases, and hence to improved chitin degradation by chitinases.

Although CBP21 was identified a number of years previously (by Suzuki et al. Biosci Biotechnol Biochem. 1998 January; 62 (1): 128-35), no biological role had previously been identified for this protein. This property of CBP21 was further investigated by generating and testing CBP21 variants with single mutations on the largely polar binding surface. Various mutants lost their ability to promote chitin degradation, while retaining considerable affinity for the polymer. Thus, binding alone is not sufficient for CBP21 functionality, and this seems to depend on specific, mostly polar interactions between the protein and crystalline chitin. This is the first time that a secreted binding protein has been shown to assist in the enzymatic degradation of an insoluble carbohydrate via non-hydrolytic disruption of the substrate (Vaaje-Kolstad et al (2005a) JBC 280 (31) 28492-7 which is incorporated herein by reference).

Various homologues of CBP21 have been shown to exist in other chitin-degrading microorganisms, suggesting a general mechanism by which chitin-binding proteins function to enhance chitinolytic activity in nature. Homologues also occur in chitinase-containing insect viruses, whose infectiousness is known to depend on chitinase efficiency. No biological role had been previously identified for those homologues.

The findings made by the present inventors thus provide a means by which chitin degradation may be promoted in an in vivo, or industrial context.

The invention thus provides a method of enhancing chitin degradation comprising exposing chitin to a non-hydrolytic chitin binding protein (CBP).

Alternatively stated, the present invention provides a method of enhancing chitin degradation comprising exposing chitin to a non-hydrolytic CBP and a chitin hydrolase, e.g. chitinase and a method of degrading chitin comprising exposing chitin to a non-hydrolytic CBP and chitin hydrolase, e.g. chitinase.

Chitin is defined herein as any polymer containing β(1-4) linked N-acetylglucosamine residues that are linked in a linear fashion. Crystalline chitin in the α form (where the chains run anti-parallel), β form (where the chains run parallel) or γ form (where there is a mixture of parallel and antiparallel chains), amorphous chitin, colloidal chitin, chitin forms in which part of the N-acetylglucosamine sugars are deacetylated & chitosan (a linear soluble polysaccharide composed of β-(1-4)-lined D-glucosamine (deacetylated unit) and N-acetyl-D-glucosamine (acetylated unit), which can be produced commercially by deacetylation of chitin) are all included within the definition of this term.

Other forms of chitin that are found in nature include copolymers with proteins and these copolymers, which include protein chitin matrices that are found in insect and crustacean cells, and any other naturally occurring or synthetic copolymers comprising chitin molecules as defined herein, are also included within the definition of "chitin".

The term "chitin" thus includes purified crystalline α, β and γ preparation, or chitin obtained or prepared from natural sources, or chitin that is present in natural sources. Examples of such natural sources include squid pen, shrimp shells, crab shells, insect cuticles and fungal cell walls. Examples of commercially available chitins are those available from sources such as France Chitin, Hov-Bio, Sigma, Sekagaku Corp. amongst others.

Degradation of chitin is caused by the enzymatic hydrolysis of the β(1-4) bonds that like the N-acetylglucosamine residues present in chitin. Depending on the number of bonds that are hydrolysed, this results in the generation of smaller fragments of chitin, N-acetylglucosamine multimers and N-acetylglucosamine monomers. Chitinases are in general responsible for this enzymatic hydrolysis.

Irrespective of any influence that exposure to an non-hydrolytic CBP has on the bonds between chitin subunits and any other members of the copolymer that might be present, degradation of chitin as referred to herein is confined to hydrolysis of the glycoside bonds that connect the β(1-4) N-acetylglucosamine bond units in a chitin substrate.

This can be carried out by a chitinase enzyme, a chitosanase (Glycoside hydrolase families 46, 75 and 80), or a lysozyme (Glycoside hydrolase families 23 and 24). The rate or degree of hydrolysis of the glycosidic bonds that connect the β(1-4) N-acetylglucosamine bond units in a chitin substrate by any of these enzymes may be enhanced in the methods of the invention. These enzymes are referred to collectively herein as chitin hydrolases.

By "enhancing the degradation of chitin", it is meant promoting or increasing the degree or rate of hydrolysis of the glycosidic bonds that connect the β(1-4) N-acetylglucosamine bond units of a chitin substrate, e.g. by chitinase, relative to the normal or usual degree or rate of hydrolysis of the glycosidic bonds that connect the β(1-4) N-acetylglucosamine bond units of a chitin substrate which is seen when said chitin substrate has not been exposed to a non-hydrolytic CBP. This can readily be determined by measuring the hydrolysis product formation e.g. at certain defined time points or by measuring the amount of undegraded chitin substrate which remains e.g. at certain defined time points. This can be carried out using methods that are well known in the art, based on e.g. determination of liberated reducing sugars (Horn, et al Carbohydrate Polymers, 56(1), 35-39. 2004 and references therein) or determination of liberated chitin fragments, e.g. by quantitative analysis of chromatograms obtained upon High Performance Liquid Chromatography (Hoell, I. et al (2005) Biochim Biophys Acta 1748(2), 180-190 Vaaje-Kolstad, G et al (2005a supra))

If the rate of hydrolysis, i.e. the number of bonds hydrolysed in a certain time period is greater when the chitin substrate has been exposed to non-hydrolytic CBP than when it has not, then the rate of degradation is considered to be enhanced.

Similarly, if the number of bonds that are hydrolysed in a certain time period is greater when the chitin substrate has been exposed to non-hydrolytic CBP than when it has not, then the degree of degradation is considered to be enhanced.

The rate or degree of degradation is also considered to be enhanced when the time taken for complete degradation of the chitin substrate is reduced when the chitin substrate has been exposed to non-hydrolytic CBP than when it has not. For example, preferably the use of non-hydrolytic CBP in accordance with the present invention will reduce the time taken for complete degradation by at least 2, 3, 4, 5, 6, 7, 8, 9 or 10 fold. In addition, the use of a non-hydrolytic CBP in accordance with the present invention can enable the complete degradation of a chitin substrate under conditions where previously complete degradation was not possible. For example, in embodiments of the invention where non-hydrolytic CBP is used in conjunction with a chitin hydrolase such as a chitinase, a chitosanase or lysozyme enzyme, then in cases where the chitin hydrolase (e.g. chitinase, chitosanase or lysozyme) enzyme alone cannot give rise to complete degradation of the substrate, the described use of a non-hydrolytic CBP can result in such complete degradation. This effect is also considered to be an enhancement of degradation.

The degree of hydrolysis is also considered to be enhanced if the overall amount of solubilisation of the chitin substrate based on exposure to a certain amount of enzyme or an enzyme cocktail is increased when said substrate has been exposed to non-hydrolytic CBP, compared to the amount that is achieved when the substrate has not been exposed to non-hydrolytic CBP.

The rate of hydrolysis is furthermore considered to be enhanced if the maximum degree of solubilization of a certain chitin-containing substrate based on exposure to a certain amount of enzyme or an enzyme cocktail is attained faster when the substrate has been exposed to non-hydrolytic CBP than when it has not been exposed to non-hydrolytic CBP.

Preferably, any such enhancement of degradation is a statistically significant one, more preferably with a probability value of <0.05. Appropriate methods of determining statistical significance are well known and described in the art and any of these may be used.

As demonstrated in the Examples, the kinetics of chitin degradation by chitinase hydrolysis of β(1-4) N-acetylglucosamine bonds when assayed in in vitro experiments are not straightforward linear kinetics. There are several kinetic phases, which in the literature are ascribed to hydrolysis of subfractions of the substrate with varying degrees of crystallinity and, thus, varying degrees of accessibility for chitinases. Sometimes, individual phases can be observed in degradation progress curves. The fast first phase is often linear and can be used to calculate initial hydrolytic rates. This phase is believed to reflect hydrolysis of the easily accessible and amorphous (i.e. the chitin chains are not orderly arranged as in a crystal, but rather disordered and thus in more contact with the solvent) regions in the substrate. During subsequent slower phases it is believed that the more recalcitrant crystalline regions of the substrate are degraded. Similar kinetics are likely to apply in respect of other chitin hydrolases.

The non-hydrolytic CBP as used herein in the methods of the invention result in a minor enhancement in the degree or rate of β(1-4) N-acetylglucosamine bond hydrolysis by the chitin hydrolase in the first, fast phase of the degradation process. However, a large effect is observed on the second slower phase. It is therefore important that if such assays with chitin hydrolases such as chitinase are performed (e.g. to determine experimentally whether a non-hydrolytic CBP has in fact functioned under the particular experimental set up to enhance the degradation of the chitin substrate, according to the definitions provided herein), a suitably long incubation time is used. As such, to detect the effect of a non-hydrolytic CBP on the rate or degree of chitin hydrolase, e.g. chitinase, degradation it is necessary to assay the rate or degree of chitin degradation after sufficiently long incubation times such that the reaction enters the subsequent, slower phase. In Example 2 (see FIG. 2) this subsequent phase is observed after the chitin (in this case β chitin), non-hydrolytic CBP (in this case CBP21) and chitinase (in this chase ChiA, B, C and G) has been incubated together for approximately 16-24 or 50 hours.

The precise kinetics will depend on many factors, such as the type of chitin, the degree of amorphousness of the chitin, the amount of enzyme present, the temperature of the pH. The degree of amorphousness will vary with the substrate source and isolation/purification process, but can be assessed by measuring the degree of crystallinity of the substrate (which is a method known in the art). Furthermore, since α-chitin is a more recalcitrant chitin form compared to the β-variant, it is anticipated that longer incubation times will be necessary in order to observe chitin degradation and hence any effect of the non-hydrolytic CBP on the rate or degree of chitin degradation.

Taking these considerations into account therefore by choosing an appropriate incubation time, the skilled person would readily be able to determine whether the degree or rate of chitin degradation is enhanced in accordance with the present invention.

The above considerations apply irrespective of the order in which the chitin is exposed to the non-hydrolytic CBP and the chitin hydrolase, e.g. chitinase, i.e. if non-hydrolytic CBP and chitin hydrolase, e.g. chitinase are not administered to the chitin substrate simultaneously, or the chitin substrate is not exposed to non-hydrolytic CBP and chitin hydrolase, e.g. chitinase, together or the chitin substrate is exposed first to non-hydrolytic CBP and then to chitin hydrolase, e.g. chitinase (for example wherein the exposure to chitin hydrolase, e.g. chitinase occurs such that the chitin hydrolase, e.g. chitinase is added to the chitin and non-hydrolytic CBP or the non-hydrolytic CBP is first removed and the chitin substrate is then exposed to the chitin hydrolase, e.g. chitinase alone), the efficacy of the method can be determined in the same way.

Comparison of the rate or degree of hydrolysis of the glycosidic bonds connecting $\beta(1-4)$ N-acetylglucosamine units by an appropriate chitin hydrolase, e.g. chitinase of a chitin substrate that has been exposed to non-hydrolytic CBP with the rate or degree of hydrolysis of the glycosidic bonds connecting $\beta(1-4)$ N-acetylglucosamine units by an appropriate chitin hydrolase, e.g. chitinase of a chitin substrate that has not been exposed to non-hydrolytic CBP will similarly show whether or not the degradation of the chitin substrate is considered to have been enhanced in accordance with the present invention.

The methods of the invention can alternatively be viewed as a method of weakening, e.g. disrupting or interfering with or modulating the structure of a chitin substrate, comprising exposing chitin to a non-hydrolytic CBP. As noted above, and as described in the Examples, it is believed that the function of e.g. CBP21 (and other non-hydrolytic CBPs) is to interact with and affect the overall structure of chitin such that it becomes more sensitive to degradation/hydrolysis by chitinases, which may be due to improved accessibility of the chitinase substrate of chitin. The structure of chitin is preferably weakened without any hydrolysis of the $\beta$1-4 N-acetylglucosamine bonds present in said chitin.

By weakened, it is meant simply that the chitin substrate is rendered more sensitive to chitin hydrolase, e.g. chitinases, i.e. it is more easily digested or hydrolysed to chitin hydrolases, e.g. chitinases. Alternatively stated, the structure of the chitin substrate is disrupted so that a structural change can be observed by electron microscopy, or such that the mechanical strength of the chitin-containing structure is reduced, or such that a reduction in crystallinity can be observed using atomic force microscopy or electron scattering analysis.

By "non-hydrolytic CBP" (CBP=chitin binding protein) it is meant a protein that binds to chitin but that itself has no hydrolytic enzyme activity, e.g. no significant or detectable chitin hydrolase, e.g. chitinase activity (it cannot hydrolyse the $\beta$-1,4-N-acetylglucosamine linkages that are present in the chitin substrate), or not significant or detectable manganese activity (it cannot hydrolyse the $\beta$-1-4-N-mannose linkages that are present in mannan). As such, the use of whole chitin hydrolase, e.g. chitinase enzymes such as ChiA, ChiB and Chi C which have chitinase activity and contain one or more chitin binding modules is explicitly excluded. Assays to detect chitinase activity (or mannanase activity) are well known in the art. The absence of chitinase activity or mannanase activity in a CBP can therefore readily be determined.

Proteins that have the ability to bind to carbohydrates are widespread in nature. In general, such proteins contain one or more carbohydrate binding modules as part of their overall structure. These proteins may for example to be structural or singalling molecules or they can be enzymes, and the overall function of the protein may be determined by domains that are present in addition to the carbohydrate binding module. A carbohydrate-binding module (CBM) is defined as contiguous amino acid sequence within a carbohydrate binding protein with a discreet fold having carbohydrate-binding activity. Indeed, chitinases are known which contain one or more chitin binding modules in addition to catalytic regions. ChiA of *Serratia Marcescens* contains a fibronectin type III-type CBM, ChiB of *Serratia Marcescens* contains a family 5 CBM and ChiC of *Serratia Marcescens* contains a family 12 and a fibronectin type III-like CBM. See Y. Bourne, B. Henrissat, *Curr. Opin. Struct. Biol.* 11, 593 (2001) for domain nomenclature.

Proteins that a bind to carbohydrates may be classified based on function and also based on structural and/or sequence characteristics. The proteins that are of particular use in the present invention are chitin binding proteins that contain chitin binding modules that are members of family 33, according to the CAZY classification system (available on the World Wide Web at cazy.org/CAZY/fam/acc CBM-.html), which is based on sequence similarities (Davies, G. J., and Henrissat, B. (2002) Biochem Soc T30, 291-297 and Y. Bourne, B. Henrissat, (2001) supra). The non-hydrolytic CBP as defined herein generally contains a carbohydrate binding module that is a member of family 33, and is thus referred to as a family 33 CBP.

All members of family 33 bind to carbohydrate structures (primarily chitin) and contain a family 33 carbohydrate binding module. In several cases, the chitin binding module makes up the whole protein, i.e. the chitin binding protein consists of or consists essentially of a single family 33 chitin binding module, that is in nature synthesised and secreted as such. However some family 33 CBMs may be fused to one or more additional non-catalytic carbohydrate binding modules (e.g. CBM family 2, CBM family 3 and CBM family 5 modules). These proteins are bi- or multi-modular non-catalytic chitin binding proteins. There is also one known example of a family 33 carbohydrate binding module that is present as an individual module within a much larger catalytic protein. This is the $\beta$1,4-mannanase protein of *Caldibacillus cellulovorans* (Sunna A et al (2000) Applied and Environmental Microbiology 66(2): 664-670).

The family 33 CBM is approximately 150-250 amino acids, e.g. 160-240, 170-230, 180-220, 190-210 amino acids in size and has a molecular weight of a approximately 20 kDa, preferably 19-21 kDa, 18-21 kDa, 19-22 kDa or 18-20 kDa in size. The size of a protein can readily be determined by standard methods that are known in the art.

The non-hydrolytic CBP is thus preferably a family 33 CBP. In general, the non-hydrolytic CBP contains a single family 33 chitin binding module. Preferably, the non-hydrolytic CBP consists of a single family 33 chitin binding module, or consists essentially of a family 33 chitin binding module.

If said non-hydrolytic CBP "consists essentially of" a family 33 chitin binding module, it is meant that additional amino acids may be present in the protein, in addition to those that make up the family 33 CBM. Preferably there are 1-3, 1-5, 1-10, 10-20, 20-30, 30-40, 40-50, 50-60, 60-70, 70-80, 80-90 and 90-100 or more additional amino acids present. These additional amino acids are in general present C terminal to the family 33 CBM.

Alternatively, the non-hydrolytic CBP can comprise a family 33 CBM. Additional modules or domains may thus be present in the protein. These additional modules or domains are non-catalytic or non-hydrolytic modules or domains and as such the CBP as a whole is non hydrolytic. The additional modules or domains can be CBMs. Examples of such modules are CBM family 2, CBM family 3 and CBM family 5 modules.

If additional domains or modules are present, they are in general found C-terminal to the family 33 CBM. The presence of additional domains or modules will of course increase the overall size of the protein.

The non-hydrolytic CBP can be or can comprise or correspond to a naturally occurring family 33 chitin binding module such as CBP21 (or to a homologue thereof from another species). It can alternatively be or can comprise or correspond to a variant of a naturally occurring non-hydrolytic family 33 CBP.

Naturally occurring non-hydrolytic CBPs that can be used in the invention include microbial (e.g. bacterial), eukaryotic (e.g. Dictyostelium) or viral non-hydrolytic CBPs. Bacterial non-hydrolytic CBPs are however preferred.

Examples of suitable non-hydrolytic CBPs are set out in Table 1:

| BACTERIA | | | |
|---|---|---|---|
| PROTEIN | ORGANISM | GENBANK/GENPEPT | |
| Cbp1 | *Alferomonas* sp. O-7 | AB063629 | BAB79619.1 |
| chitin binding protein ChbA | *Bacillus amyloliquefaciens* ALKO 2718 | AF181997 | AAG09957.1 |
| BA_3348 | *Bacillus anthracis* str. A2012 | NC_003995 | NP_656708.1 |
| BA2827 | *Bacillus anthracis* str. Ames | AE017033 | AAP26659.1 |
| | | NC_003997 | NP_845173.1 |
| BA2793 | *Bacillus anthracis* str. Ames | AE017032 | AAP26628.1 |
| | | NC_003997 | NP_845142.1 |
| GBAA2827 | *Bacillus anthracis* str. Ames 0581 | AE017334 | AAT31944.1 |
| GBAA2793 | *Bacillus anthracis* str. Ames 0581 | AE017334 | AAT31910.1 |
| BAS2636 | *Bacillus anthracis* str. Sterne | AE017225 | AAT54946.1 |
| BAS2604 | *Bacillus anthracis* str. Sterne | AE017225 | AAT54914.1 |
| BCE2855 | *Bacillus cereus* ATCC 10987 | AE017273 | AAS41767.1 |
| | | NC_003909 | NP_979159.1 |
| BCE2824 | *Bacillus cereus* ATCC 10987 | AE017273 | AAS41736.1 |
| | | NC_003909 | NP_979128.1 |
| BC2827 | *Bacillus cereus* ATCC 14579 | AE017007 | AAP09778.1 |
| | | NC_004722 | NP_832577.1 |
| BC2798 | *Bacillus cereus* ATCC 14579 | AE017007 | AAP09751.1 |
| | | NC_004722 | NP_832550.1 |
| pE33L466_0276 (ChbA) | *Bacillus cereus* E33L | CP000040 | AAY60428.1 |
| BTZK2523 (ChB) | *Bacillus cereus* ZK | CP000001 | AAU17736.1 |
| BTZK2552 (ChB) | *Bacillus cereus* ZK | CP000001 | AAU17707.1 |
| ABC1161 | *Bacillus clausii* KSM-K16 | AP006627 | BAD63699.1 |
| BH1303 | *Bacillus halodurans* C-125 | AP001511 | BAB05022.1 |
| | | NC_002570 | NP_242169.1 |
| BLi00521 or BL00145 | *Bacillus licheniformis* DSM 13 ATCC 14580 | CP000002 | AAU22121.1 |
| | | AE017333 | AAU39477.1 |
| BT9727_2586 (ChB) | *Bacillus thuringiensis* serovar *konkukian* str. 97-27 | AE017355 | AAT61310.1 |
| BT9727_2556 (ChB) | *Bacillus thuringiensis* serovar *konkukian* str. 97-27 | AE017355 | AAT61323.1 |
| BMAA1785 | *Burkholderia mallei* ATCC 23344 | CP000011 | AAU45854.1 |
| BMA2896 | *Burkholderia mallei* ATCC 23344 | CP000010 | AAU48386.1 |
| BURPS1710b_0114 | *Burkholderia pseudomallei* 1710b | CP000124 | ABA49030.1 |
| BURPS1710b_A2047 | *Burkholderia pseudomallei* 1710b | CP000125 | ABA53645.1 |
| BPSL3340 | *Burkholderia pseudomallei* K96243 | BX571965 | CAH37353.1 |
| BPSS0493 | *Burkholderia pseudomallei* K96243 | BX571966 | CAH37950.1 |
| Bcep18194_C6726 | *Burkholderia* sp. 383 | CP000150 | ABB05775.1 |
| BTH_Ii1925 | *Burkholderia thailandensis* E264; ATCC 700388 | CP000085 | ABC34637.1 |
| BTH_I3219 | *Burkholderia thailandensis* E264; ATCC 700388 | CP000086 | ABC38514.1 |
| -1,4-mannanase (ManA) | *Caldibacillus cellulovorans* | AF163837 | AAF22274.1 |
| CV0554 | *Chromobacterium violaceum* ATCC 12472 | AE016911 | AAQ58230.1 |
| | | NC_005085 | NP_900224.1 |
| CV0553 | *Chromobacterium violaceum* ATCC 12472 | AE016911 | AAQ58229.1 |
| | | NC_005085 | NP_900223.1 |
| CV2592 (CpbD) | *Chromobacterium violaceum* ATCC 12472 | AE016919 | AAQ60262.1 |
| | | NC_005085 | NP_902262.1 |
| CV3489 | *Chromobaterium violaceum* ATCC 12472 | AE016922 | AAQ61150.1 |
| | | NC_005085 | NP_903159.1 |
| CV3323 (CbpD1) | *Chromobacterium violaceum* ATCC 12472 | AE016921 | AAQ60987.1 |
| | | NC_005085 | NP_902993.1 |
| EF0362 | *Enterococcus faecalis* V583 | AE016948 | AAO80225.1 |
| | | NC_004668 | NP_814154.1 |
| Sequence 4287 from patent U.S. Pat. No. 6583275 | *Enterococcus faecium* | — | AAQ43729.1 |
| FTL_1408 | *Francisella tularensis* subsp. *holarctica* LVS | AM233362 | CAJ79847.1 |
| FTT0816c | *Francisella tularensis* subsp. *tularensis* Schu 4 | AJ749949 | CAG45449.1 |
| HCH_00807 | *Hahella chejuensis* KCTC 2396 | CP000155 | ABC27701.1 |
| HCH_03973 | *Hahella chejuensis* KCTC 2396 | CP000155 | ABC30692.1 |

BACTERIA

| PROTEIN | ORGANISM | GENBANK/GENPEPT | |
|---|---|---|---|
| Ip_1697 | *Lactobacillus plantarum* WCFS1 | AL935256 | CAD64126.1 |
|  |  | NC_004567 | NP_785278.1 |
| LSA1008 | *Lactobacillus sakei* subsp. sakei 23K | CR936503 | CAI55310.1 |
| YucG | *Lactococcus lactis* subsp. lactis IL 1403 | AE006425 | AAK06049.1 |
|  |  | NC_002662 | NP_268108.1 |
| lpp0257 | *Legionella pneumophila* Paris | CR628336 | CAH11404.1 |
| Lin2611 | *Listeria innocua* | AL596173 | CAC97838.1 |
|  |  | NC_003212 | NP_471941.1 |
| Lmo2467 | *Listeria monocytogenes* EGD-e | AL591983 | CAD00545.1 |
|  |  | NC_003210 | NP_465990.1 |
| LMOf2365_2440 | *Listeria monocytogenes* str. 4b F2365 | AE017330 | AAT05205.1 |
| OB0810 | *Oceanobacillus iheyensis* HTE831 | AP004595 | BAC12766.1 |
|  |  | NC_004193 | NP_691731.1 |
| PBPRB0312 | *Photobacterium profundum* SS9 | CR378676 | CAG22185.1 |
| plu2352 | *Photorhabdus luminescens* subsp. *laumondii* TTO1 | BX571866 | CAE14645.1 |
|  |  | NC_005126 | NP_929598.1 |
| Sequence 6555 from patent U.S. Pat. No. 6605709 | *Proteus mirabilis* | — | AAR43285.1 |
| chitin-binding protein ChiB | *Pseudoalteromonas* sp. S9 | AF007895 | AAC79666.1 |
| chitin-binding protein (CbpD; PA0852) | *Pseudomonas aeruginosa* PAO1 | AE004520 | AAG04241.1 |
|  |  | NC_002516 | NP_249543.1 |
| chitin-binding protein (CbpD) | *Pseudomonas aeruginosa* PAO25 | AF196565 | AAF12807.1 |
| PFL_2090 | *Pseudomonas fluorescens* Pf-5 | CR000076 | AAY91365.1 |
| Pfl_3569 | *Pseudomonas fluorescens* PfO-1 | CP000094 | ABA75307.1 |
| Psyr_2856 | *Pseudomonas syringae* pv. syringae B728a | CP000075 | AAY37892.1 |
| PSPTO2978 | *Pseudomonas syringae* pv. tomato str. DC3000 | AE016866 | AAO56470.1 |
|  |  | NC_004578 | NP_792775.1 |
| RF_0708 | *Rickettsia felis* URRWXCal2 | CP000053 | AAY61559.1 |
| chitin-binding protein (CbpA) | *Saccharophagus degradans* 2-40 | BK001045 | DAA01337.1 |
| ORF | *Sallnivibrio costicola* 5SM-1 | AY207003 | AAP42509.1 |
| chitin-binding protein (Cbp21) | *Serratia marcescens* 2170 | AB015998 | BAA31569.1 |
| chitin-binding protein (Cbp21) | *Serratia marcescens* BJL200 | AY665558 | AAU88202.1 |
| ORF2 | *Serratia marcescens* KCTC2172 | L38484 | AAC37123.1 |
| SO1072 | *Shewanella oneidensis* MR-1 | AE015551 | AAN54144.1 |
|  |  | NC_004347 | NP_716699.1 |
| SG1515 (possible fragment) | *Sodalis glossinidius* str. 'morsitans' | AP008232 | BAE74790.1 |
| SAV6560 | *Streptomyces avermitilis* MA-4680 | AP005047 | BAC74271.1 |
|  |  | NC_003155 | NP_827736.1 |
| SAV2168 | *Streptomyces avermitilis* MA-4680 | AP005029 | BAC69879.1 |
|  |  | NC_003155 | NP_823344.1 |
| SAV5223 (Chb) | *Streptomyces avermitilis* MA-4680 | AP005042 | BAC72935.1 |
|  |  | NC_003155 | NP_826400.1 |
| SAV2254 (CelS2) | *Streptomyces avermitilis* MA-4680 | AP005030 | BAC69965.1 |
|  |  | NC_003155 | NP_823430.1 |
| SCO7225 or SC2H12.24 | *Streptomyces coelicolor* A3(2) | AL359215 | CAB94648.1 |
|  |  | NC_003888 | NP_631281.1 |
| SCO6345 or SC3A7.13 | *Streptomyces coelicolor* A3(2) | AL031155 | CAA20076.1 |
|  |  | NC_003888 | NP_630437.1 |
| SCO2833 (Chb) | *Streptomyces coelicolor* A3(2) | AL136058 | CAB65563.1 |
|  |  | NC_003888 | NP_627062.1 |
| SCO0643 or SCF91.03c | *Streptomyces coelicolor* A3(2) | AL132973 | CAB61160.1 |
|  |  | NC_003888 | NP_624952.1 |
| SCO0481 or SCF80.02 | *Streptomyces coelicolor* A3(2) | AB017013 | BAA75647.1 |
|  |  | AL121719 | CAB57190.1 |
|  |  | NC_003888 | NP_624799.1 |
| SCO1734 or SCI11.23 | *Streptomyces coelicolor* A3(2) | AL096849 | CAB50949.1 |
|  |  | NC_003888 | NP_626007.1 |
| CelS2 (SCO1188 or SCG11A.19) | *Streptomyces coelicolor* A3(2) | AL133210 | CAB61600.1 |
|  |  | NC_003888 | NP_625478.1 |
| chitin binding protein | *Streptomyces griseus* | AB023785 | BAA86267.1 |
| cellulose binding protein (ORF2) | *Streptomyces halstedii* | U51222 | AAC45430.1 |
| chitin-binding protein | *Streptomyces olivaceoviridis* ATCC 11238 | X78535 | CAA55284.1 |
| chitin binding protein (Chb2) | *Streptomyces retculi* | Y14315 | CAA74695.1 |
| chitin-binding protein (Cbp1) | *Streptomyces thermoviolaceus* OPC-520 | AB110078 | BAD01591.1 |
| chitin-binding protein celS2 | *Streptomyces viridosporus* | AF126376 | AAD27623.1 |
| Tfu_1665 (E8) | *Thermobifida fusca* YX | CP000088 | AAZ55700.1 |
| Tfu_1268 (E7) | *Thermobifida fusca* YX | CP000088 | AAZ55306.1 |
| VCA0140 | *Vibrio cholerae* N16961 | AE004355 | AAF96053.1 |
|  |  | NC_002506 | NP_232540.1 |
| VCA0811 | *Vibrio cholerae* N16961 | AE004409 | AAF96709.1 |
|  |  | NC_002506 | NP_233197.1 |
| VFA0143 | *Vibrio fischeri* ES114 | CP000021 | AAW87213.1 |
| VFA0013 | *Vibrio fischeri* ES114 | CP000021 | AAW87083.1 |
| VPA0092 | *Vibrio parahaemolyticus* RIMD 2210633 | AP005084 | BAC61435.1 |
|  |  | NC_004605 | NP_799602.1 |

-continued

| BACTERIA | | | |
|---|---|---|---|
| PROTEIN | ORGANISM | GENBANK/GENPEPT | |
| VPA1598 | *Vibrio parahaemolyticus* RIMD 2210633 | AP005089 | BAC62941.1 |
| | | NC_004605 | NP_801108.1 |
| VV21258 | *Vibrio vulnificus* CMCP6 | AE016812 | AAO08152.1 |
| | | NC_004460 | NP_763162.1 |
| VV20044 | *Vibrio vulnificus* CMCP6 | AE016808 | AAO07021.1 |
| | | NC_004460 | NP_762031.1 |
| VVA0086 | *Vibrio vulnificus* YJ016 | AP005344 | BAC96112.1 |
| | | NC_005140 | NP_936142.1 |
| VVA0551 | *Vibiro vulnificus* YJ016 | AP005346 | BAC96577.1 |
| | | NC_005140 | NP_936607.1 |
| ChiY | *Yersinia enterocolitica* (type 0:8) WA-314 | AJ344214 | CAC83040.2 |
| YP0706 | *Yersinia pestis* biovar Medievalis str. 91001 | AE017129 | AAS60972.1 |
| | | NC_005810 | NP_992095.1 |
| YPO3227 | *Yersinia pestis* CO92 | AJ414156 | CAC92462.1 |
| | | NC_003143 | NP_406699.1 |
| Y0962 | *Yersinia pestis* KIM | AE013699 | AAM84543.1 |
| | | NC_004088 | NP_668292.1 |
| YPTB3366 | *Yersinia pseudotuberculosis* IP 32953 | BX936398 | CAH22604.1 |
| YPTB0899 | *Yersinia pseudotuberculosis* IP 32953 | BX936398 | CAH20139.1 |

| EUKARYOTA | | | |
|---|---|---|---|
| PROTEIN | ORGANISM | GENBANK/GENPEPT | |
| ORF-26 | Agrotis segetum nucleopolyhedrovirus | DQ123841 | AAZ38192.1 |
| spheroidin-like protein (Gp 37) | Autographa californica nucleopolyhedrovirus | L22858 | AAA66694.1 |
| | | D00583 | BAA00461.1 |
| | | NC_001623 | NP_054094.1 |
| fusolin | Bombyx mori nuclear polyhedrosis virus | U55071 | AAB47606.1 |
| | | L33180 | AAC63737.1 |
| | | NC_001962 | NP_047468.1 |
| spheroidin | Choristoneura biennis entomopoxvirus | M34140 | AAA42887.1 |

| VIRUSES | | | |
|---|---|---|---|
| PROTEIN | ORGANISM | GENBANK/GENPEPT | |
| ORF-26 | Agrotis segetum nucleopolyhedrovirus | DQ123841 | AAZ38192.1 |
| Spheroidin-like protein (Gp 37) | Autographa californica nucleopolyhedrovirus | D00583 | BAA00461.1 |
| | | L22858 | AAA66694.1 |
| | | NC_001623 | NP_054094.1 |
| fusolin | Bombyx mori nuclear polyhedrosis virus | U55071 | AAB47606.1 |
| | | NC_001962 | NP_047468.1 |
| | | L33180 | AAC63737.1 |
| spheroidin | Choristoneur biennis entomopoxvirus | M341140 | AAA42887.1 |
| ORF60 | Choristoneura furniferana defective nucleopolyhedrovirus | AY327402 | AAQ91667.1 |
| | | NC_005137 | NP_932669.1 |
| spindle-like protein | Choristoneura furniferana nuclear polyhedrosis virus | U26734 | AAC55636.1 |
| | | NC_004778 | NP_848371.1 |
| GP37 (ORF-67 GP37) | Chrysodeixis chalcites nucleopolyhedrovirus | AY864330 | AAY83998.1 |
| ORF57 | Epiphyas postvittana nucleopolyhedrovirus | AY043265 | AAK85621.1 |
| | | NC_003083 | NP_203226.1 |
| GP37 | Helicoverpa armigera single nucleocapsid polyhedrovirus | AF266696 | AAK57880.1 |
| | | AF303045 | AAK96305.1 |
| | | NC_003094 | NP_203613.1 |
| ORF59 | Helicoverpa zea nucleopolyhedrovirus | AF334030 | AAL56204.1 |
| | | NC_003349 | NP_542682.1 |
| gp37 | Heliocoverpa armigera nucleopolyhedrovirus G4 | AF271059 | AAG53801.1 |
| | | NC_002654 | NP_075127.1 |
| fusolin | Heliothis armigera entomopoxvirus | L08077 | AAA92858.1 |
| HynVgp086 (slp) | Hyphantria cunea nucleopolyhedrovirus | AP009046 | BAE72375.1 |
| Gp37 protein | Leucania separata nuclear polyhedrosis virus | AB009614 | BAA24259.1 |
| fusolin-like protein | Lymantria dispar nucleopolyhedrovirus | U38895 | AAB07702.1 |
| | | AF081810 | AAC70254.1 |
| | | NC_001973 | NP_047705.1 |

-continued

VIRUSES

| PROTEIN | ORGANISM | GENBANK/GENPEPT | |
|---|---|---|---|
| gp37 protein | Mamestra brassicae nucleopolyhedrovirus | AF108960 | AAD45231.1 |
| ORF 37 (Gp37) | Mamestra configurata nucleopolyhedrovirus A | U59461 | AAM09145.1 |
| | | AF539999 | AAQ11056.1 |
| Gp37 | Mamestra configurata nucleopolyhedrovirus B | AY126275 | AAM95019.1 |
| | | NC_004117 | NP_689207.1 |
| spheroidin-like protein (Gp 37) | Orgyia pseudotsugata nuclear polyhedrosis virus | U75930 | AAC59068.1 |
| | | D13306 | BAA02566.1 |
| | | NC_001875 | NP_046225.1 |
| enhancing factor | Pseudaletia separata entomopoxvirus | D50590 | BAA09138.1 |
| ORF25 | Spodoptera exigua nucleopolyhedrovirus | AF169823 | AAF33555.1 |
| | | NC_002169 | NP_037785.1 |
| gp37 (fragment) | Spodoptera frugiperda MNPV | AY250076 | AAP79107.1 |
| ubiquitin GP37 fusion protein | Spodoptera litura nucleopolyhedrovirus G2 | AF325155 | AAL01718.1 |
| | | NC_003102 | NP_258300.1 |
| gp37 | Trichoplusia ni single nucleopolyhedrovirus | DQ017380 | AAZ67435.1 |
| fusolin | unidentified entomopoxvirus | X77616 | CAA54706.1 |
| ORF107 | Xestia c-nigrum granulovirus | AF162221 | AAF05221.1 |
| | | NC_002331 | NP_059255.1 |

Bacterial non-hydrolytic CBPs can be from any appropriate source but are preferably from a species selected from the group consisting of *Bacillus, Chromobacterium, Enterococcus, Francisella, Hahella, Lactobacillus, Lactococcus, Legionella, Listeria, Oceanobacillus, Photobacterium, Photothabdus, Proteus, Pseudoalteromonas, Pseudomonos, Rickettsia, Saccharophagus, Salinvibrio, Serratia, Shewanella, Sodalis, Streptomyces, Thermobifida, Vibrio* and *Yersinia*.

Examples of specific non-hydrolytic CBPs are CBP 21 of *Serratia Marescens* (SEQ ID NO: 1, MNKTSRTLLSLGLL-SAAMFGVSQQANAHGYVESPASRAYQCK-LQLNTQCGSVQYEPQSVEGLKGFPQAG-PADGHIASADKSTFFELDQQTPTRWNKLNLKTGPNS FTWKLTARHSTTSWRYFITKPNWDASQPLTRA SFDLTPFCQFNDGGAIPAAQVTHQCNI-PADRSGSHVILAVWDIADTANAFYQAIDVNLSK, where amino acid residues 1 to 27 correspond to the leader peptide that is necessary for secretion of the protein in a natural system and amino acids 28-197 correspond to the mature protein), ChbA of *B. amyloliquefaciens* (Chu et al, Microbiology. 2001 July; 147 (Pt 7): 1793-803) CHB1, 2 & 3 of *Streptomyces* (Svergun et al., Biochemistry. 2000 Sep. 5; 39 (35): 10677-83, Zeltins et al., Eur J Biochem. 1997 Jun. 1; 246 (2): 557-64, Zeltins et al., Anal Biochem. 1995 Nov. 1; 231 (2): 287-94, Schnellmann et al., Mol Microbiol. 1994 September; 13 (5): 807-19, Kolbe et al., Microbioloy. 1998 May; 144 (Pt 5): 1291-7, Saito et al., Appl Environ Microbiol. 2001 March; 67 (3): 1268-73), CBP1 of *Alteramonas* (Tsujibo et al, Appl. Environm. Microbiol. 68: 263-270 (2002)). All of these references are incorporated herein by reference.

The non-hydrolytic CBP can thus be or correspond to or comprise a naturally occurring CBP (such as CBP21, ChbA, CHB1, 2 & 3 and CBP1) in that it is a CBP (e.g. a family 33 CBP) that is found in nature.

Alternatively, the non-hydrolytic CBP can be derived from a naturally occurring protein which contains an appropriate CBM, such as the β1,4 mannanase referred to above, or any other family 33 CBP that contains modules or domains that are present in addition to the family 33 CBM. In the latter case, the appropriate CBM for use as a non-hydrolytic CBP in accordance with the present invention can be obtained by any appropriate method. For example, the sequence that encodes the CBM can be determined and expressed in isolation from the rest of the protein using standard molecular biology techniques that are known in the art. Alternatively, for example, the CBM can be removed from the native protein by for example proteolytic cleavage.

Variants, derivatives or fragments of naturally occurring CBPs or CBMs can also be used, providing that these variants, derivatives or fragments retain the functional property of the CBP in that they bind to chitin and enhance the degradation of chitin or weaken chitin as described herein, for example by causing disruption to the chitin substrate, i.e. they should be considered to be functionally equivalent variants. As noted elsewhere herein, the property can be tested for in a straightforward manner.

The non-hydrolytic CBP as defined herein has the property of being able to bind to at least one type of chitin. It must also have the property, which has been demonstrated for CBP21, of enhancing the degradation of chitin or weakening chitin. Whether or not a protein has the ability to bind to chitin and to enhance the degradation of chitin or weaken chitin by for example causing disruption to the chitin substrate can readily be determined by straightforward assays that have been described in the art e.g. by using the assays that are set out in Examples 2-3 and Vaaje-Kolstad et al ((2005a) supra). For example the rate of chitin degradation by chitin hydrolase, e.g. Chitinase in the presence and absence of the putative non-hydrolytic CBP or following exposure to the putative non-hydrolytic CBP can be compared.

Variants include or comprise naturally occurring variants of the non-hydrolytic CBP as defined herein such as comparable proteins or homologues found in other species or more particularly variants found within other microorganisms, which have the functional properties of a non-hydrolytic CBP as defined elsewhere herein.

Variants of the naturally occurring non-hydrolytic CBPs as defined herein can also be generated synthetically e.g. by using standard molecular biology techniques that are known in the art, for example standard mutagenesis techniques such as site directed or random mutagenesis. Such variants further include or comprise proteins having at least 70, 80, 85, 90, 91, 92, 93, 94, 95, 96, 97, 98 or 99% sequence similarity or identity with a naturally occurring CBP or CBM at the amino acid level.

When variants are generated, it should be noted that appropriate residues to modify depend on the properties that are being sought in such a variant. In the case that a variant having the same binding or enhancing or weakening properties of the non-hydrolytic CBP is being sought, the residues are in general those residues that are not involved in the interaction of the non-hydrolytic CBP with the chitin substrate. Preferably the residues that are modified are residues that are not involved with the property of enhancing or weakening degradation exhibited by the non-hydrolytic CBP (although of course it is possible that this property could be further improved by mutating these residues).

On the other hand, it will be appreciated by a person skilled in the art that residues that are crucial for the functionality of CBP21 (see Example 4), or analogous or corresponding residues in CBP21-like proteins may be mutated with the aim of further improving the function of the non-hydrolytic CBP. This could be done by standard protein engineering techniques or by techniques based on random mutagenesis followed by screening, all techniques that are well known in the art. Attempts to improve the function of a non-hydrolytic CBP may include improving the binding and disrupting ability of this non-hydrolytic CBP towards other types of insoluble carbohydrate polymers than the polymer(s) on which the CBP acts naturally. Such alternative polymers include carbohydrate containing copolymers, e.g. protein-carbohydrate co-polymers.

For Example, the case of CBP21, several residues have been shown to be important in the binding of CBP21 to chitin and more specifically to the ability of CBP21 to enhance the degradation of chitin. Several mutations have been shown not to affect binding, but to affect the ability of CBP21 to enhance the degradation of chitin. These residues are preferably not modified relative to the wild type CBP21 sequence as set out in SEQ ID NO: 1, if the aim is to modify e.g. the stability of the non-hydrolytic CBP (for example under process conditions), but these residues may be targeted if one's aim is to improve or change the non-hydrolytic CBP functional properties.

A person skilled in the art will recognize the potential of using the CBP framework to create variants that are optimised for other insoluble polymeric polysaccharide substrates (e.g. other forms of chitin or cellulose), or insoluble carbohydrate-containing co-polymers.

Preferred variants of CBP21 retain one or more and preferably all of: a tyrosine residue at position 54, a glutamic acid residue at position 55, a glutamic acid residue at position 60, a histidine residue at position 114, an aspartic acid residue at position 182 and an asparagine at position 185 (sequence numbering according to SEQ ID NO: 1).

Further preferred variants of CBP21 retain one or more and preferably all of a tyrosine residue at position 54, a glutamic acid residue at position 55, a glutamic acid residue at position 60, a histidine residue at position 114 and an aspartic acid residue at position 182 (sequence number according to SEQ ID NO: 1).

In connection with amino acid sequences, "sequence similarity", preferably "sequence identity", refers to sequences which have the stated value when assessed using e.g. using the SWISS-PROT protein sequence databank using FASTA pep-cmp with a variable pamfactor, and gap creation penalty set at 12.0 and gap extension penalty set at 4.0, and a window of 2 amino acids). Sequence identity at a particular residue is intended to include identical residues which have simply been derivatized.

Preferred "variants" include those to which instead of the naturally occurring amino acid the amino acid which appears in the sequence is a structural analogue thereof. Amino acids used in the sequence may also be derivatized or modified, e.g. labelled, glycosylated or methylated, providing the function of the non-hydrolytic CBP is not significantly adversely affected.

Variants refers to peptides related to, or derived from the above described amino acid sequences, where the amino acid sequence has been modified by single or multiple amino acid (e.g. at 1 to 10, e.g. 1 to 5, preferably 1 or 2 residues) substitution, addition and/or deletion or chemical modification, including deglycosylation or glycosylation, but which nonetheless retain functional activity, insofar as they bind to chitin and enhance the degradation of chitin.

Within the meaning of "addition" variants are included amino and/or carboxyl terminal fusion proteins or polypeptides, comprising an additional protein or polypeptide or other molecule fused to the non-hydrolytic CBP sequence. Carboxyl terminal fusions are preferred. It must of course be ensured that any such fusion to non-hydrolytic CBP does not adversely affect the functional properties required for use in the methods of the invention as set out elsewhere herein.

"Substitution" variants preferably involve the replacement of one or more amino acids with the same number of amino acids and making conservative substitutions. Such functionally-equivalent variants mentioned above include in particular naturally occurring biological variations (e.g. found in other microbial species) and derivatives prepared using known techniques. In particular functionally equivalent variants of the non-hydrolytic CBPs described herein extend to non-hydrolytic CBPs which are functional in (or present in), or derived from different genera or species than the specific CBP molecules mentioned herein.

Variants such as those described above can be generated in any appropriate manner using techniques which are known and described in the art, for example using standard recombinant DNA technology.

Derivative of non-hydrolytic CBPs as defined herein my also be used. By derivative it is meant a non-hydrolytic CBP or variant thereof which instead of the naturally occurring amino acid, contains a structural analogue of that amino acid. Derivatisation, modification (e.g. labelling, glycosylation, methylation) may also occur as long as the function of the non-hydrolytic CBP is not adversely affected.

Fragments of the non-hydrolytic CBPs may also be used as long as the function of the non-hydrolytic CBP required for use in the present invention is not adversely affected by the deletion of one or more amino acids from said non-hydrolytic CBP, i.e. the ability of the non-hydrolytic CBP to bind to chitin and also to enhance the degradation of chitin for example by causing disruption to the chitin substrate.

The fragment may be a truncated version of a non-hydrolytic CBP, e.g. CBP 21 e.g. C terminal deletion of 1, 2, 3, 4, 5, amino acids although in general N terminal deletions of CBP21 should be avoided.

In the most preferred embodiment, the non-hydrolytic CBP is or comprises the CBP21 protein from *Serratia marcescens* having the amino acid sequence set out in SEQ ID No:1. Functional variants, derivatives and fragments of this protein are also preferred.

By "exposing" the chitin to the non-hydrolytic CBP, it is meant that the non-hydrolytic CBP and chitin are brought into contact in an appropriate context and under appropriate conditions so as to allow the two components to interact or bind to each other. It has been shown for CBP21 that for this non-hydrolytic CBP, binding to chitin is necessary for its effect in enhancing chitin degradation (Vaaje-Kolstad et al 2005a, supra) and it is believed that the enhancement of chitin degradation depends on the formation of the appropriate bonds between these two components.

The chitin substrate is thus mixed with, or contacted with the non-hydrolytic CBP under suitable conditions so as to allow this interaction to take place. Suitable contact must therefore be made between the non-hydrolytic CBP and the chitin substrate so as to allow these two components to interact. Thus, the non-hydrolytic CBP may simply be brought into contact with the chitin substrate for example by adding it directly to the chitin substrate. Conveniently, the non-hydrolytic CBP may be present in a liquid medium which is applied to the chitin substrate. In general, the non-hydrolytic CBP will be present in an aqueous solution, although any appropriate conditions can be used. The following description sets out conditions that can be used, but it should be noted that any appropriate conditions can be used, and the step of "exposing" the chitin substrate to the non-hydrolytic CBP can take place in any appropriate context, e.g. in a transgenic plant as discussed in more detail below, or in the context of a medical or agricultural treatment, where the non-hydrolytic CBP is administered to a patient or a plant.

In a preferred embodiment the non-hydrolytic CBP is present in a buffer such as a phosphate buffer, e.g. a sodium phosphate buffer. Suitable concentration ranges for such a buffer are 1-100 mM. The non-hydrolytic CBP can be present in the solution at any suitable concentration, such as a concentration of 0.001-1.0 mg/ml, e.g. 0.01-0.1 mg/ml or 0.05-0.5 mg/ml.

Preferably the chitin substrate is exposed to the non-hydrolytic CBP, e.g. the chitin substrate and the non-hydrolytic CBP are incubated with each other, for a period of 12 or 24 hours or more, e.g. 36 or 48 hours or more, or 3, 4, 5, 6, 7, 8, 9, 10, 11, 12, 13, 14 days or more. This incubation is in general carried out at or about 37° C., although appropriate temperatures for optimizing the enhancement of chitin degradation can readily be determined by the skilled person in the art. For example, the temperature can be in the range of 36-38° C. or 35-38° C.

It will be appreciated by the person skilled in the art that the necessary incubation times, pH, temperature, substrate concentrations and CBP21 concentrations are not independent of each other. Thus, a large range of conditions can be envisaged, which can easily be evaluated by a person skilled in the art.

Preferably the chitin substrate is exposed to the non-hydrolytic CBP, e.g. the chitin substrate and the non-hydrolytic CBP are incubated with each other, at an appropriate pH, for example at a pH in the range of 5.5 to 7, or 6 to 6.5, although appropriate pHs for optimizing the enhancement of chitin degradation can readily be determined by the skilled person in the art. Preferably the pH is in the range of 6.2-6.4 or 6.25-6.35. The preferred pH is about pH 6.3.

Preferably the incubation is carried out without agitation, i.e. without stirring or disturbing the mixture. This may reduce any adherence of chitin substrate to the walls of the vessel.

The exposure of the chitin substrate to the non-hydrolytic CBP can occur in vitro in any appropriate vessel, e.g. by mixing together the chitin substrate and the non-hydrolytic CBP in an appropriate medium (e.g. a solution, such as an aqueous solution) or by applying the non-hydrolytic CBP to the chitin substrate (e.g. by applying the non-hydrolytic CBP in a solution to a chitin substrate).

As indicated above, in an alternative embodiment of the invention a chitin hydrolase, e.g. chitinase, chitosanase or lysozyme may be used in combination with the non-hydrolytic CBP under appropriate conditions to enhance chitin degradation. Thus, the chitin substrate can be exposed simultaneously to the non-hydrolytic CBP and the chitin hydrolase, e.g. chitinase, chitosanase or lysozyme or else the chitin substrate is exposed to the non-hydrolytic CBP and the chitin hydrolase, e.g. chitinase, chitosanase or lysozyme sequentially, in either order. It is preferred that the CBP is added before the chitin hydrolase, e.g. chitinase, chitosanase or lysozyme.

Any chitin hydrolase, e.g. chitinase, chitosanase or lysozyme that is able to degrade the glycosidic bonds in the chitin substrate may be added. Such degradation may be complete or partial. For example, the activity of some chitin hydrolase, e.g. chitinases on chitin substrates is not strong enough to result in complete degradation of the substrate. This is particularly the case for chitinases such as ChiG from *Streptomyces coelicolor* that do not have their own CBM, or chitinases such as ChiB. In this case, the use of a non-hydrolytic CBP in accordance with the present invention can result in enhanced chitin degradation and preferentially result in complete degradation that was not previously possible. Examples of appropriate chitinases include all enzymes and putative enzymes listed in the CAZY database under glycoside hydrolase families 18 and 19.

In addition, chitosanases (glycoside hydrolase families 46, 75 and 80) and lysozymes (glycoside hydrolase families 23 and 24) may be appropriate.

Other enzymes may also be added in addition to or as an alternative to the chitin hydrolytic enzymes discussed above, depending on the nature of the chitin substrate that is to be degraded. For example, if the chitin to be degraded is a copolymer which contains protein, proteases may also be added. Suitable examples include Alcalase, Neutrase, Papain and other broad-specificity proteolytic enzymes. In each experimental set-up the suitability of proteases will need to be checked, especially if other enzymes (e.g. chitinases), which may be destroyed by some of the available proteases, are present simultaneously. It must be noted that disruption of chitinous parts of a chitin-containing co-polymers may facilitate enzymatic degradation of the non-chitinous parts, even if no chitinase is present simultaneously. If the non-chitinous parts consist of non-protein compounds, other appropriate enzymes may be added.

In the embodiments including the use of chitin hydrolase, e.g. chitinases, the chitin substrate is mixed with, or contacted with non-hydrolytic CBP and chitin hydrolase, e.g. chitinase under suitable conditions so as to allow the appropriate interaction or interactions to take place between the chitin hydrolase, e.g. chitinase enzyme and the chitin substrate and between the non-hydrolytic CBP and the chitin substrate the enzymatic hydrolysis of the β1-4 N-acetyl glucosamine bonds to occur. As discussed above, in relation to the contact between the CBP and the chitin substrate, suitable contact must be made between the components of this system. Thus, the non-hydrolytic CBP and chitin hydrolase, e.g. chitinase may simply be brought into contact with the chitin substrate for example by adding them directly in the chitin substrate. Conveniently, the non-hydrolytic CBP and the chitin hydrolase, e.g. chitinase may be present in a liquid medium which is applied to the chitin substrate. In general, the non-hydrolytic CBP and the chitin hydrolase, e.g. chitinase will be present in an aqueous solution, although any appropriate conditions can be used.

In a preferred embodiment the non-hydrolytic CBP and the chitin hydrolase, e.g. chitinase are present in a buffer such as a phosphate buffer, e.g. a sodium phosphate buffer. Suitable concentration ranges for such a buffer are 1-100 mM. The non-hydrolytic CBP can be present in the solution at any suitable concentration, such as a concentration of 0.001-1.0 mg/ml, e.g. 0.01-0.1 mg/ml or 0.05-0.5 mg/ml.

Preferably the chitin substrate is exposed to the non-hydrolytic CBP and the chitin hydrolase, e.g. chitinase e.g. the chitin substrate and the non-hydrolytic CBP are incubated with each other, for a period of 12 or 24 hours or more, e.g. 36 or 48 hours or more, or 3, 4, 5, 6, 6, 8, 9, 10, 11, 12, 13, 14 days or more. This incubation is in general carried out at or about 37° C., although appropriate temperatures for optimizing the enhancement of chitin degradation can readily be determined by the skilled person in the art. For example, the temperature can be in the range of 36-38° C. or 35-39° C.

It will be appreciated by the person skilled in the art that the necessary incubation times, pH, temperature, substrate concentrations and CBP21 concentrations are not independent of each other. Thus, a large range of conditions can be envisaged, which can easily be evaluated by a person skilled in the art.

Preferably the chitin substrate is exposed to the non-hydrolytic CBP and the chitin hydrolase, e.g. chitinase, e.g. the chitin substrate, the non-hydrolytic CBP and the chitin hydrolase, e.g. chitinase are incubated with each other, at a pH in the range of 5.5 to 7, or 6 to 6.5, although appropriate pHs for optimizing the enhancement of chitin degradation can readily be determined by the skilled person in the art. Preferably the pH is in the range of 6.2-6.4 or 6.25-6.35. The preferred pH is about pH 6.3.

Preferably the incubation is carried out without agitation, i.e. without stirring or disturbing the mixture. This may reduce any adherence of chitin substrate to the walls of the vessel.

The exposure of the chitin substrate to the chitin hydrolase, e.g. chitinase and the non-hydrolytic CBP can occur in vitro in any appropriate vessel, e.g. by mixing together the chitin substrate and the chitin hydrolase, e.g. chitinase and the non-hydrolytic CBP in an appropriate medium (e.g. a solution, such as an aqueous solution) or by applying the chitin hydrolase, e.g. chitinase and the non-hydrolytic CBP to the chitin substrate (e.g. by applying the chitin hydrolase, e.g. chitinase and the non-hydrolytic CBP in a solution to a chitin substrate).

If the chitin is exposed first to the non-hydrolytic CBP and then to the chitin hydrolase, e.g. chitinase (i.e. the chitin substrate is not simultaneously exposed to the non-hydrolytic CBP and the chitin hydrolase, e.g. chitinase), the chitinase may simply be added to the chitin that has been exposed to the CBP, without the removal of the non-hydrolytic CBP, e.g. by supplementing the non-hydrolytic CBP containing solution with chitinase or mixing a chitinase containing solution with the non-hydrolytic CBP containing solution.

Alternatively, the non-hydrolytic CBP, e.g. in a non-hydrolytic CBP containing solution, may be removed from the chitin substrate and replaced with a chitin hydrolase, e.g. chitinase containing solution. In each case, the chitin is exposed first to the non-hydrolytic CBP and then to the chitinase.

Appropriate forms of non-hydrolytic CBP and variants etc., thereof, for use in the methods of the present invention are described above. Thus, the non-hydrolytic CBP that is present, e.g. in the solution, can be in many different forms, and isolated, extracted or purified from various different sources or synthesised by various different means.

For example, the non-hydrolytic CBP (for variant, etc., thereof) can be a synthetic non-hydrolytic CBP that has been chemically synthesised. Chemical syntheses may be performed by methods well known in the art involving, in the case of peptides, cyclic sets of reactions of selection deprotection of the functional groups of a terminal amino acid and coupling of selectively protected amino acid residues, followed finally by complete deprotection of all functional groups. Synthesis may be performed in solution or on a solid support using suitable solid phases known in the art, such as the well known Merrifield solid phase synthesis procedure. Preferably the non-hydrolytic CBPs for use in the invention are substantially purified, e.g. pyrogen-free, e.g. more than 70%, especially preferably more than 90% pure (as assessed for example, in the case of peptides or proteins, by an appropriate technique such as peptide mapping, sequencing or chromatography). Purification may be performed for example by chromatography (e.g. HPLC, size-exclusion, ion-exchange, affinity, hydrophobic interaction, reverse-phase) or capillary electrophoresis.

Recombinant expression of proteins is also well known in the art and an appropriate nucleic acid sequence can be used to express a non-hydrolytic CBP (or variant, etc., thereof) for subsequent expression and optional purification using techniques that are well known in the art. For example, an appropriate nucleic acid sequence can be operably linked to a promoter for expression of the non-hydrolytic CBP (or variant, etc., thereof) in bacterial cells, e.g. E. coli. It may be convenient to express the non-hydrolytic CBP under the control of an inducible promoter, in which case the expression of the non-hydrolytic CBP will be induced in culture to cause expression.

As the non-hydrolytic CBPs are in general secreted, it is generally possible to purify them from the supernatant or periplasmic fractions of host cells using techniques that are known in the art (e.g. as described in Vaaje-Kolstad et al) to provide the source of the non-hydrolytic CBP. The purified protein can then be mixed with an appropriate liquid or solution for administration or addition to the chitin substrate that is to be exposed thereto. This approach is equally applicable to recombinant bacteria and to bacteria that naturally synthesise and secrete non-hydrolytic CBPs.

These proteins are secreted and in general contain a leader sequence that is responsible for secretion. Optionally therefore, genes encoding leader peptide-free non-hydrolytic CBPs may be fused to DNA sequences endcoding leader peptides of choice to ensure efficient secretion by certain host bacteria. Alternatively, CBP genes may be clones without leader peptide and produced intracellularly.

Alternatively, the supernatant or growth medium in which the bacteria which naturally produces the non-hydrolytic CBP or which is expressing a recombinant non-hydrolytic CBP can be used as the source of the non-hydrolytic CBP. If the bacteria naturally express the non-hydrolytic CBP, it may be necessary to first induce the secretion of the CBP by growing or culturing the bacteria in the presence of a suitable inducer of synthesis such as chitin.

Partial purification or concentration of the non-hydrolytic CBP from the supernatant or growth medium in which the bacteria which naturally produces the non-hydrolytic CBP or which is expressing a recombinant non-hydrolytic CBP is growing is also possible. Suitable examples of how this might be carried out to achieve the required concentration or purity of non-hydrolytic CBP are well known in the art. Chitin degrading organisms can be grown in media containing chitin as the only carbon source. Secreted proteins can be harvested by precipitating all the proteins present in the medium, followed by renaturation and isolation through general protein separation methods (e.g. electrophoresis). A second option is to collect the chitin from the growth medium after a period of growth, an then elute all bound proteins (which should be chitinases and chitin binding proteins) off the chitin. This can be done by first washing the chitin with a wash buffer (e.g. 50 mM sodium phosphate, pH 6.3) and then eluting the chitin bound proteins off with an elution buffer (a buffer either low or high in pH or with a high salt concentration). The protein eluted from the chitin can the be separated by standard protein separation methods.

The appropriate non-hydrolytic CBP to be used in these methods depends on the particular type of chitin or chitin containing copolymer that is to be degraded and can readily be determined by a person skilled in the art. For example, CBP21 binds only to β-chitin and would therefore by an appropriate non-hydrolytic CBP to use if the methods of the invention were to be applied to β-chitin.

ChbB from *B amyloliquifaciens* as described in Chu et al (supra) also binds to β-chitin and would therefore also be an appropriate non-hydrolytic CBP to use if the methods of the invention were to be applied to β-chitin.

CHB1, CHB2 and CHB3 have all been isolated from *S olivaceovirides* (Svergun et al, Zeltins et al, Schnellman et al Kolbe et al, Saito et al supra). The binding preferences of these three proteins have been determined and CHB1 and CHB2 bind preferably to α-chitin, whereas CHB3 binds to both α and β chitin. CBP1 from *Alteromonas* as described by Tsujibo et al binds to both α and β chitin, with a preference for the α form.

It is clear that a suitable or appropriate non-hydrolytic CBP to use in the methods of the invention has to be determined based on the ability of the non-hydrolytic CBP to interact with and disrupt the chitin substrate that is to be degraded, and that the current choice of the non-hydrolytic CBP for a particular chitin substrate is important. As described above, different non-hydrolytic CBPs bind to different chitin substrates, and binding is essential for the non-hydrolytic CBP to enhance the degradation of chitin.

A first step in identifying an appropriate non-hydrolytic CBP for use in the method is therefore to determine what non-hydrolytic CBPs bind to the chitin substrate of interest. This can be carried out by referring to binding studies that have been carried out in the prior art, e.g. if the nature of the chitin substrate that is to be degraded has been characterised. Alternatively, appropriate binding studies can readily be performed by the skilled man using techniques that are known in the art.

Such binding studies can also be performed if the nature of the chitin substrate that is to be degraded has not bee fully characterised. Again, this can readily be performed by the skilled man using techniques that are known in the art.

Those non-hydrolytic CBPs that bind to the chitin substrate that is to be degraded can then be tested for their ability to enhance the degradation of that substrate e.g. using assays as set out in the Examples. Modifications to the assays may be required depending on the particular chitin substrate that is to be degraded. For example, very long incubation times and/or higher enzyme concentrations are required if the substrate is α chitin, since the crystalline part of this chitin variant is very recalcitrant compared to β chitin or amorphous chitin.

It is similarly possible to use these techniques to identify whether a variant of a non-hydrolytic CBP would be suitable for use in the methods of the invention.

As discussed above, multiple chitinases exist in nature and they vary in their activity towards different chitin substrates. As such, the particular chitinase that is to be used in the methods of the invention can also be selected based on its ability to degrade the particular chitin substrate that is to be degraded. The properties of chitinases have been documented (e.g. Hollis, T et al (1997) Arch. Biochem. Biophys. 344, 335-342 and Suzuki, K., et al (1998) Biosci. Biotech. 62, 128-135] and chitinases can be tested based on routine assays that are well known to the person skilled in the art. Any type of chitinase e.g. a naturally occurring, recombinant, or synthetic chitinase may be used. Preferred chitinases are microbial chitinases and plant chitinases.

It is clear from the specific example of CBP21 that a single non-hydrolytic CBP can influence the degradation of a chitin substrate by multiple chitinases e.g. chitinases belonging to family 18 of glycoside hydrolases (e.g. ChiA, B, C) or family 19 of glycoside hydrolases (e.g. ChiG) and thus such various different chitinases or combinations of chitinases can be used with any one non-hydrolytic CBP in the methods of the invention. With any chitin substrate that is to be degraded, once a suitable non-hydrolytic CBP has been identified, one or more chitinases may be chosen to hydrolyse the glycosidic bonds connecting the β(1-4) N-acetylglucosamine sugars.

Preferred combinations are CBP21 (or variants, fragments or derivatives thereof) with one or more of ChiA, ChiB, ChiC and ChiG. This is a preferred combination for the degradation of chitin substrates that contain or consist of β chitin. For alpha chitin, a preferred combination would consist of CHB1 or CHB2 (Svergun et al, Zeltins et al, Schnellman et al Kolbe et al supra) or another alpha-chitin binding CBP21 analogue, combined with one or more of ChiA, ChiB, ChiC and ChiG. In principle, any chitinase could be tried in combination with any CBP that targets the "correct substrate".

More than one, i.e. multiple chitin hydrolase, e.g. chitinases can be used to hydrolyse the glycosidic bonds connection the β(1-4) N-acetylglucosamine sugars. Multiple chitin hydrolase, e.g. chitinases can be added simultaneously or sequentially to the chitin substrate. Preferably 2, 3, 4, 5 or 6 or more different chitin hydrolase, e.g. chitinases can be used.

It is also possible to use more than one non-hydrolytic CBP in the methods of the invention. In other words, the chitin substrate that is to be degraded can be exposed to one or more non-hydrolytic CBP or to multiple (e.g. 2, 3, 4 or more) non-hydrolytic CBPs. The non-hydrolytic CBPs may have binding specificity to and function on the same type of chitin, or they may have different binding specificities and functions from each other. The latter may be appropriate if a chitin substrate that is to be degraded contains more than on type of chitin (for example γ chitin).

Based on the above considerations, it can be seen that a further embodiment of the invention relates to an assay method for identifying a non-hydrolytic CBP, or determining whether a protein is a non-hydrolytic CBP. In such an assay method the putative noon-hydrolytic CBP is exposed to chitin e.g. under conditions that are described above and the effect of exposure to this protein is assessed, e.g. as described above. If chitin is weakened or an improvement in the rate or degree of chitin degradation is observed after exposure to this protein, compared to in the absence of the exposure to the protein, the protein is considered to be non-hydrolytic CBP.

This invention has applications in a number of different fields and, due to the ability of the non-hydrolytic CBP to enhance chitin degradation, can be used to improve any method which is based on the action of chitinolytic enzymes (chitin hydrolase enzymes).

Thus, the methods of the invention can be used to improve or enhance chitin degradation in the conversion of a chitin-containing biomass to chitin fragments or N-acetylglucosamine.

N-acetylglucosamine has several applications (e.g. as discussed below) and thus the methods of the invention can be used to produce GlcNac for use in any of these applications. Currently, ClcNAc is most often produced by acid hydrolysis of chitin (a linear polymer of GlcNAc) extracted from crab and shrimp shells. The methods of the present invention thus provide an alternative and improved method of producing GlcNac. Similarly, chitin fragments (chito-oligosaccharides)

also have a variety of applications (e.g. as discussed below), and thus the methods of the invention can be used to produce chitin fragments (chito-oligosaccharides) for use in any of these applications.

As indicated above, GlcNAc has several known applications. For example, N-acetylglucosamine and its derivative glucosamine are sold as a health product, e.g. as a food supplement. Although the actions of supplemental glucosamine have yet to be clarified, it is thought to play a role in the promotion and maintenance of the structure and function of cartilage in the joints of the body. It may also have anti-inflammatory properties. For example, the glucosamine-containing glycosaminoglycan hyaluronic acid is vital for the function of articular cartilage.

In addition, during the progression of osteoarthritis, exogenous-glucosamine may have a beneficial role. Glucosamine has also been found to have antioxidant activity and to be beneficial in animal models of experimental arthritis. Glucosamine may be used for the treatment and prevention of osteoarthritis. Glucosamine may be used for the treatment and prevention of osteoarthritis, either by itself or in combination with chondroitin sulfate.

As referred to above, fragments of chitin and their derivatives have a variety of applications, (M. G. Peter, in Biopolymers, Vol. 6: Polysaccharides II (A. Steinbüchel, Ed.), Weinheim: Wiley VCH, 2002, pp. 481-574). For example, they have been shown to act as immune stimulants, and to cause chemotactic migration of polymorphonuclear cells. They are also known to elicit defence responses in plants and function as signalling molecules in certain cellular processes in humans (e.g. stimulation of bone cell growth). See also Sven Bahrke et al, Biomacromolecules 3:696-704 (2002) and reference therein.

Fragments resulting from the degradation of chitin may be used directly or they may be used as building blocks to generate for example biologically active glycoconjugates. Biological activities of chitin fragments include roles as signalling molecules, for example in plants and mammals, e.g. humans. Other roles include immune stimulation, promotion of bone cell (chondrocyte) growth, morphogenetic activity and elicitation of defence response in plants. Certain fragments may inhibit chitinases, before or after chemical functionalization. Chitinase inhibitors are of interest because many plague organisms (malaria parasite, fungi, nematodes) need chitinases for growth.

Chitin fragments are good building blocks for synthesizing compounds that potentially interfere with enzymes involved in chitin catabolism or metabolism. Since many plague organisms contain chitin whereas humans do not, chitin catabolism and metabolism are very interesting target areas for development of drugs, fungicides, pesticides. The use as building blocks means that one may couple fragments resulting from the degradation of chitin to other compounds in order to give them a desirable activity. One example is a synthetic chitinase inhibitor described in detail by Vaaje-Kolstad et al. (Interactions of a family 18 chitinase with the designed inhibitor HM508 and its degradation product, chitobiono-delta-lactone; J Biol Chem. 2004 Jan. 30; 279 (5): 3612-9). Here, a dimer of GlcNAc has been made active as a chitinase inhibitor by coupling it to another chemical group.

As noted above, since many plague organisms contain chitin whereas humans do not, chitin catabolism and metabolism are very interesting target areas for development of drugs, fungicides, pesticides. Thus, the disruption of the cell walls and/or membranes and/or skeletons of appropriate pathogens and parasites has been a useful therapeutic strategy against pathogens (in particular fungi) and parasites. For example, Amphotericin B and fluconazole exert their antifungal activity by affecting membrane steroids. Various antifungal therapeutics have been developed but fungal infections of mammals, in particular humans, have increasingly become responsible for life-threatening disorders. Furthermore, toxicity associated with known antifungal drugs can cause serious adverse side effects, and mortality rates of certain fungal infections such as systemic candidiasis remain high despite Amphotericin B treatment.

Examples of fungal species and parasites include *Candida, Aspergillus, Cryptococcus, Histoplasma, Coccidioides* and *Pneumocystis*. These pathogens are particularly dangerous in immunocompromised individuals, such as patients with AIDS, patients undergoing chemotherapy, and immunosuppressed organ transplant patients.

Fungi also present a serious problem to farmers as they are very common causative agents of infectious disease of crop plants. Phytopathogenic fungi cause devastating epidemics, and cause annual crop yield losses and crop failures. The effects of fungi are not specific to a few plant species, but attack all of the known species of flowering plants, and also to attack crop plants and trees.

Traditionally the strategies that are used to control plant disease include the use of disease resistant cultivars. Such cultivars can be selected or developed by plant breeders e.g. by breeding to incorporate natural resistance mechanisms into the crops.

There are however disadvantages with this approach as the genetic sources of this natural resistance are often associated with other undesirable properties and in order to recreate the desired background, extensive backcrossing and introgression is needed. This is compounded by the fact that the resistance mechanism(s) are often polygenic. In view of these problems, the steps of improving disease resistance by conventional breeding are expensive in terms of both time and money.

As an alternative to conventional breeding techniques, the use of recombinant DNA technology has provided the possibility of introducing disease resistance using transgenes. For example, an isolated resistance gene or other useful gene in plant defence mechanisms can be used to transform a plant.

This new technology has not however prevented crop disease epidemics and additional strategies should be contemplated to supplement the conventional breeding method and existing genetic engineering strategies.

As noted above, chitin is present in fungal cell walls and the walls and membranes of other pathogens and parasites, and chitinases have antibiotic action against such organism. It should therefore be possible to combat plant fungal infections and diseases in plants caused by other chitin containing pathogens, e.g. insects or nematodes by taking advantage of the newly identified properties of non-hydrolytic CBPs to improve or enhance chitin degradation or to weaken chitin.

Therefore in a further aspect, the present invention relates to a composition comprising a non-hydrolytic CBP as defined herein and a pharmaceutically or agriculturally acceptable carrier, diluent or excipient. Said compositions (and indeed other non-hydrolytic CBP containing compositions as defined herein) can be used to enhance the degradation of chitin or to weaken chitin. Said uses can be carried out in vitro, e.g. in a bioreactor or test tube, or in vivo, e.g. in a plant, animal, microorganism, etc, i.e. in any environment where chitin is present.

As the composition contains a non-hydrolytic CBP, the ability of this protein to enhance the degradation of chitin, which is key component of fungi (and other plant pathogens such as nematodes and insects), will adversely affect the growth of said fungi (and other plant pathogens such as nematodes and insects).

In addition to a non-hydrolytic CBP, the composition may further comprise other active ingredients such as chitin hydrolase, e.g. chitinase as defined herein and/or a further fungicidal or pathicidal agent. Suitable agents for inclusion in a composition that is to be used in the treatment of mammals will be known to a person skilled in the art and can be selected depending on the nature of the fungus or other pathogen which is to be treated by the composition. Suitable fungal agents include amphotericin B, nystatin, pimaricin, 5-fluorocytosine; azole derivatives such as fluconazole, ketoconazole, clotrimazole, miconazole, econazole, butoconazole, oxiconazole, sulconazole, terconazole, itraconazole and tioconazole; allylamines-thiocarbamates such as tolnaftate, naftifme and terbinafme; griseofulvin; ciclopirox olamine; haloprogin; undecylenic acid; and benzoic acid. The fact that synergistic anti-fungal effects may be obtained by combining the applicant of chitinolytic enzymes with application of anti-fungal agents such as gliotoxin, flusilazole, miconazole, captan and benomyl is documented in the literature (Lorito M, et al Microbiology. 1994 March; 140 (Pt 3): 623-9).

Suitable additional fungicidal agents for inclusion in a composition that is to be used in the treatment of plants will be known to a person skilled in the art and can be selected depending on the nature of the fungus which is to be treated by the composition. Suitable agents include fungal cell membrane affecting compounds selected from the group consisting of sterollsynthesis inhibiting fungicides, antifungal peptide antibiotics, zeamatin and proteins that are serologically related to zeamatin, and antifungal lipid lytic enzymes. Alternative additional components of the composition include antifungal polyene macrolide antibiotics, antifungal epithiodiketopiperizine antibiotics, fungal cell wall biosynthesis inhibitors such as chitin synthetase inhibitors and β glucan synthetase inhibitors. Such compounds are described in U.S. Pat. No. 6,512,166 which is incorporated herein by reference. Such compositions can be formulated according to any of the conventional methods known in the art and widely described in the literature. Thus, the active ingredient (i.e. a non-hydrolytic CBP) may be incorporated, optionally together with other active substances (such as chitin hydrolase, e.g. chitinases and/or other fungicidal or pathicidal agents, examples of which are as described above), with one or more conventional carriers, diluents and/or excipients appropriate for the particular use for a composition, e.g., agriculturally acceptable carriers for agricultural uses and pharmaceutically acceptable carriers for medicinal uses, to produce conventional preparations which are suitable or can be made suitable for administration such as powders, sachets, cachets, elixirs, suspensions, emulsions, solutions, syrups, ointments, sterile injectable solutions, sterile packaged powders, and the like. They may be formulated as liquids (solutions or suspensions) or as solids. Preferably the pharmaceutical composition comprising the non-hydrolytic CBP is prepared in a form appropriate for topical application.

Examples of suitable carriers, excipients, and diluents are lactose, dextrose, sucrose, maltose, glucose, sorbitol, mannitol, starches, gum acacia, calcium phosphate, aglinates, tragacanth, gelatin, calcium silicate, polyvinylpyrrolidone, water syrup, water, water/ethanol, water/glycol, water/polyethylene, glycol propylene glycol, methyl cellulose, methylhydroxybenzoates, propyl hydroxybenzoates, talc, magnesium stearate, mineral oil or fatty substances such as hard fat or suitable mixtures thereof. The compositions may additionally include lubricating agents, wetting agents, emulsifying agents, suspending agents, preserving agents, sweetening agents, flavouring agents, and the like. The compositions of the invention may be formulated so as to provide quick, sustained or delayed release of the active ingredient after administration to the patient or plant by employing procedures well known in the art.

As described above, preferably the composition is in a form suitable for topical administration and suitable carriers may be present at any appropriate concentration, but exemplary concentrations are from 1% to 20% and preferably from 5% to 10%.

Suitable doses of the non-hydrolytic CBP and the other active ingredients (if included) will vary from plant to plant and from patient to patient and will also depend on the nature of the particular infection (as the type of chitin or co-polymer may be different). Suitable doses can be determined by the person skilled in the art or the physician in accordance with the weight, age and sex of the patient, the severity of the fungal infection, and according to the nature and age of the plant to be treated Exemplary unit doses are: 0.1 to 50 mg, of the active ingredient. Unit doses will normally be administered once or more times a day, for example 2, 3 or 4 times a day, more usually 1 to 5 times a day, such that the daily dose is normally in the range of 0.1 to 50 mg, for example 0.1 to 5 mg for a 70 kg adult, that is in the range of approximately 0.001 to 1 mg/kg/day, more usually 0.005 to 0.2 mg/kg/day.

If chitin hydrolase, e.g. chitinase is present in the composition, since free water is needed for their activity, water must be present at the time of function. This can be accomplished, for example, by making up the chitin hydrolase, e.g. chitinases as aqueous solutions or by making a formulation as a dry powder and applying the powder with the enzyme becoming active once water becomes available, e.g., from rain or saliva. Water is thus a preferred vehicle where components are soluble in it. Organic solvents can also be used and may be required in some cases if a solution is desired. Suspensions can also be employed. Most polyene macrolide antibiotics have poor water solubility and are therefore normally formulated as dispersions or suspensions for application or applied as a powder. The chitin synthetase inhibitors may also be applied as a powder.

For medicinal purposes (i.e., human and veterinary therapy) the composition comprising a non-hydrolytic CBP is preferably administered topically e.g. to the skin of a human or non-human animal. Administration can also be, at least in some instances, via parenteral injection, e.g., intraperitoneally; this administration route is particularly useful where the immune system has been compromised since immune-deficient humans and individuals will inactivate enzymatic proteins more slowly than normal individuals.

Thus, a yet further aspect of the invention provides a method for treating or preventing disease in a plant, wherein said disease is caused by a chitin containing microorganism or pathogen, for example a fungus, insect or nematode, comprising contacting the chitin containing microorganism or pathogen or contacting the plant to be protected with an effective amount of non-hydrolytic CBP as defined herein.

A preferred embodiment of the invention provides a method for treating or preventing fungal infection in a plant, comprising contacting the fungus or a plant to be protected from the fungus with an antifungal effective amount of a non-hydrolytic CBP as defined herein.

Any of the compositions that are described above can be used in such a method.

The compositions and method of the invention can be used to prevent or treat any disease in a plant which is caused by a chitin containing microorganism or pathogen.

A yet further aspect of the invention provides a method for treating or preventing disease in an animal, wherein said disease is caused by a chitin containing microorganism or pathogen, for example a fungus, insect or nematode, comprising administering to a subject in need of such a treatment with an effective amount of a non-hydrolytic CBP as defined herein.

A preferred embodiment of the invention provides a method for treating or preventing fungal infection in an animal, comprising administering to a subject in need of such a treatment an antifungal effective amount of a non-hydrolytic CBP as defined herein.

Any of the compositions that are described above can be used in such a method. The modes of administration of the non-hydrolytic CBP can be any appropriate mode as discussed above in connection with the composition.

The method is generally carried out in a mammal. Any mammal may be treated, for example humans and any livestock, domestic or laboratory animal. Specific examples include mice, rats, pigs, cats, dogs, sheep, rabbits, cows and monkeys. Preferably however the mammal is human.

The composition and method described above can be used to prevent or treat fungal infection wherein the fungal species is from genera including *Fusarium, Gliociadium, Rhizoctonia, Trichoderma, Uncinula, Ustilago, Erysiphe, Botrytis, Saccharomyces, Sclerotium, Candida, Aspergillus* and *Alternaria*.

The composition and method described above can also be used to prevent infection or damage by insects and nematodes, e.g. nematodes belonging to the genera *Globodera, Meloidogyne* and *Heterodera*. Nematode eggs are of special interest because they contain a chitin layer in their shells. Strategies aimed at insects should normally focus on chitinous layers in the gastrointestinal tract and on the cuticle.

As used herein "treating" refers to the reduction or alleviation, preferably to normal levels, of one or more of the symptoms of disease (e.g. fungal infection) For example, such treatment might result in e.g. the reduction of infectivity of the chitin containing microorganism or pathogen, for example a fungus, insect or nematode, or an overall reduction in the amount of detectable chitin containing microorganism or pathogen, for example a fungus, insect or nematode. "Preventing" refers to absolute prevention, i.e. absence of detectable fungus and/or maintenance of normal levels of detectable chitin containing microorganism or pathogen, for example a fungus, insect or nematode, or reduction or alleviation of the extent of timing (e.g. delaying) of the infection with said chitin containing microorganism or pathogen, for example a fungus, insect or nematode.

An "effective amount" is an amount effective to inhibit the infection, germination or growth of a relevant chitin containing microorganism or pathogen, for example a fungus, insect or nematode, relative to the infection, germination or growth that is seen in the absence of any such treatment.

As the present invention provides the first demonstration of the chitin degradation enhancing properties of non-hydrolytic CBPs, it can be seen that such non-hydrolytic CBPs as described herein are targets in the control of chitin metabolism, for example in chitin containing plague organisms. It is known that several plague organisms (e.g. insects, nematodes and malarial parasites) require chitin degradation during their life cycles. Thus, the present invention further provides a method for combating or treating diseases caused by chitin containing plague organisms such as those described above, which method comprises the administration to an organism of an agent which targets a non hydrolytic CBP as defined herein. Examples of suitable agents include antibodies direct to non hydrolytic CBPs as defined herein, or agents that serve to reduce the expression of non hydrolytic CBPs e.g. at the transcriptional or translational level (e.g. antisense molecules, ribozymes).

As noted above, chitin is present in fungal cell walls and the walls and membranes of other pathogens and parasites, and chitinases have antibiotic action against such organisms. It should therefore be possible to combat plant fungal infections and diseases in plants caused by other chitin containing pathogens, e.g. insects or nematodes by taking advantage of the newly identified properties of non-hydrolytic CBPs to improve, enhance or weaken chitin degradation. Thus, the present invention provides utility in such exemplary applications as enhancing disease resistance in plants, particularly crop plants such as maize.

Plants expressing chitinases have been previously shown to have improved resistance to infection with chitin containing pathogens (see for example, Benhamou, N., K. Broglie, et al. (1993). "Antifungal Effect on Bean Endochitinase on Rhizoctonia-Solani—Ultrastructural-Changes and Cytochemical Aspects of Chitin Breakdown." Canadian Journal of Microbiology 39(3): 318-328, Bolar, J. P., J. L. Norelli, et al. (2000). "Expression of endochitinase from Trichoderma harzianum in transgenic apple increases resistance to apple scab and reduces vigor." PHYTOPATHOLOGY 90(1): 72-77, Herrera-Estrella, A. and I. Chet (1999). Chitinases in biological control Chitin and Chitinases. P. Jollès and R. A. A. Muzzarelli, Birkhäuser: 171-84 and Ding, X., B. Gopalakrishnan, et al. (1998). "Insect resistance of transgenic tobacco expressing an insect chitinase gene." Transgenic Res 7(2): 77-84.

Plants that have been engineered to express non-hydrolytic CBPs are therefore likely to similarly have improved or probably even better resistance to chitin containing pathogens.

A further embodiment of the invention relates to a transgenic plant comprising an exogenous nucleic acid molecule comprising a sequence encoding a non-hydrolytic CBP as defined herein.

The transgenic plant may further comprise an exogenous nucleic acid molecule comprising a sequence encoding a chitin hydrolytic, e.g. chitinase enzyme, as defined herein.

These plants preferably have improved or enhanced resistance to chitin containing pathogens in that they show reduced rates of infectivity when compared to non-transgenic or wild type plants of the same species (i.e. exposure to higher doses, or quantities or exposure to more virulent chitin containing pathogens are required in order for the plants to become infected with chitin containing pathogens). Alternatively, improved resistance to chitin containing pathogens can be apparent in diminishment of the pathogen when compared to non-transgenic or wildtype plants of the same species.

Without being bound by theory, this may come about by any means, including, but not limited to improved lysis of the pathogen (e.g. fungal pathogen) through weakening of the cell wall.

By "transgenic plant" it is meant a plant which comprises within its genome an exogenous polynucleotide. Generally, the exogenous polynucleotide is integrated, preferably stably integrated within the genome such that the polynucleotide is passed on to successive generations. The exogenous polynucleotide may be integrated into the genome alone or as part of a recombinant expression cassette. "Transgenic" is used herein to include any cell, cell line, callus, tissue, plant part or plant, the genotype of which has been altered by the presence of exogenous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

By "encoding" it is meant that the nucleic acid comprises the necessary information for translation into the specified protein to be carried out. A nucleic acid molecule encoding a protein may contain additional non-translated sequences (e.g. introns).

Exogenous in reference to a nucleic acid or protein molecule is one that originates from a different species, or if from the same species, is substantially modified from its native form in composition and/or genomic locus by deliberate human intervention. For example, a microbial sequence is an exogenous sequence when found in a transgenic plant.

Generally the exogenous nucleic acid sequence will be operably linked, i.e. functionally linked to a regulatory sequence.

The term "regulatory sequence" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences. Preferably, the regulatory elements are ones that operational in plants, for example, a plant promoter and plant polyadenylation recognition sequence.

As used herein, the term "promoter" refers to a nucleotide sequence capable of controlling the expression of a coding sequence or RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate elements of the promoter or a heterologous element inserted to enhance the level or tissue-specificity of a promoter.

Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". Exemplary plant promoters include, but are not limited to, those that are obtained from plants, plant viruses, and bacteria which comprise genes expressed in plant cells such *Agrobacterium* and *Rhizobium*. Examples of promoters under development control include promoters that preferentially initiate transcription in certain tissues, such as leaves, roots, or seeds.

New promoters of various types useful in plant cells are constantly being discovered; numerous examples may be found in the compilation by Okamuro and Goldberg (1989) Biochemistry of Plants 15:1-82. It is further recognized that since in most cases the exact boundaries of regulatory sequences have not been completely defined, nucleic acid fragments of different lengths may have identical promoter activity.

Preferably, the plant is a monocot or dicot. Most preferably, the plant is a crop plant, e.g. *Arabidopsis* ssp., *Euphorbia* ssp. particularly *Euphorbia pulcherrima*, *Begonia* x *cheimantha*, *Begonia* x *hiemalis*, *Begionia* x *tuberhybrida*, *Begonia semperflorens*, *Campanula* ssp., *Brassica* ssp., or *Lycopersium esculenium*.

The nucleic acid sequence as referred to herein encodes any non-hydrolytic CBP as defined herein. Most of the appropriate non-hydrolytic CBPs are microbial in origin and it is well known that expression of microbial sequences can be enhanced by modifying the codons that are used such that expression is enhanced in plants. This is particularly useful in the case of expressing a microbial sequence such as the sequence encoding CBP21 in a plant in view of the fact that codon preferences differ in microorganisms and plants. In a preferred embodiment therefore, the nucleic acid sequence contains codons that are preferred for expression in plants (plant high use codons).

Methods for making transgenic plants are well known in the art. The nucleic acid molecule containing the exogenous sequence is typically inserted into a vector e.g. with a regulatory sequence. Typical vectors that are useful for expression of genes in plants are well known in the art and include vectors derived from the tumor induced (Ti) plasmid of *Agrobacterium tumefaciens*. The non-hydrolytic CBP and the chitin hydrolytic enzyme, e.g. chitnase can be on the same or different vector, under the control of the same or different regulatory sequences.

The vector comprising the sequences from a polynucleotide of the present invention will typically also comprise a marker gene, which confers a selectable phenotype of plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicides basta, the nptII gene encodes resistance to the antibiotics kanamycin and geneticin, and the ALS gene encodes resistance to the herbicide chlorsulfuron.

The method of transformation/transfection is not critical to the instant invention; various methods of transformation or transfection are currently available. As newer methods are available to transform crops they may be directly applied. Accordingly, a wide variety of methods have been developed to insert a DNA sequence into the transformation/transfection may be employed.

Any plant may be transformed. In this manner, genetically modified plants, plant cells, plant tissue, seed, and the like can be obtained. Transformation protocols may vary depending on the type of plant cell, i.e. monocot or dicot, target for transformation. Suitable methods of transforming plant cells include microinjection (Crossway et al., (1986) BioTechniques 4:320-334), electroporation (Riggs et al. (1986) Proc. Natl. Acad. Sci. USA 83:5602-5606, *Agrobacterium* mediated transformation (Hinchee et al., (1988) Biotechnology 6:915-921), direct gene transfer (Paszkowski et al., (1984) EMBO J. 3:2717-2722), and ballistic particle acceleration (see, for example, Sanford et al., U.S. Pat. No. 4,945,050; Tomes et al., "Direct DNA Transfer into Intact Plant Cells via Microprojectile Bombardment" In Gamborg and Phillips (Eds.) Plant Cell, Tissue and Organ Culture: Fundamental Methods, Springer-Verlag, Berlin (1995); and McCabe et al., (1988) Biotechnology 6:923-926). Also see, Weissinger et al., (1988) Annual Rev. Genet. 22:421-477; Sanford et al., (1987) Particular Science and Technology 5:27-37 (onion); Christou et al., (1988) Plant Physiol. 87:671-674 (soybean); McCabe et al., (1988) Bio/Technology 6:923-926 (soybean); Datta et al., (1990) Biotechnology 8:736-740 (rice); Klein et al., (1988) Proc. Natl. Acad. Sci. USA 85:4305-4309 (maize); Klein et al., (1988) Biotechnology 6:559-563 (maize); Tomes et al., "Direct DNA Transfer into Intact Plant Cells via Microprojectile Bombardment" in Gamborg and Phillips (Eds.) Plant Cell, Tissue and Organ Culture: Fundamental Methods, Springer-Verlag, Berlin (1995) (maize); Klein et al., (1988) Plant Physiol. 91:440-444 (maize) Fromm et al., (1990) Biotechnology 8:833-839 (maize); Hooydaas-Van Slogteren & Hooykaas (1984) Nature (London) 311:763-764; Bytebier et al., (1985) In The Experimental Manipulation of Ovule Tissues ed. G. P. Chapman et al., pp. 197-209. Longman, N.Y. (pollen); Kaeppler et al., (1990) Plant Cell Reports 9:415-418; and Kaeppler et al., (1992) Theor. Apply Genet. 84:560-566 (whisker-mediated transformation); D'Halluin et al., (1992) Plant Cell 4:1495-1505 (electroporation); Li et al., (1993) Plant Cell Reports 12:250-255 and Christou and Ford (1995) Annals of Botany 75:745-750 (maize via *Agrobacterium tumefaciens*); all of which are herein incorporated by reference.

The cells, which have been transformed, may be grown into plants in accordance with conventional ways. See, for example, McCormick et al. (1986) Plant Cell Reports, 5:81-84. These plants may then be grown, and either pollinated with the same transformed strain or different strains, and the resulting hybrid having the desired phenotypic characteristic identified. Two or more generations may be grown to ensure that the subject phenotypic characteristics is stable maintained and inherited and then seeds harvested to ensure the desired phenotype or other property has been achieved. One of skill will recognize that after the exogenous nucleic acid molecule is stably incorporated in transgenic plants and confirmed to be operable, it can be introduced into other plants by sexual crossing. Any of number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In see propagated crops, mature transgenic plants can be self crossed to produce a homozygous inbred plant. The inbred plant produces seed containing the newly introduced heterologous nucleic acid. These seeds can be grown to produce plans that would produce the selected phenotype.

Parts obtained from the regenerated plant, such as flowers, seeds, leaves, branches, fruit, and the like are included in the invention, provided that these parts comprise cells comprising the exogenous nucleic acid molecule. Progeny and variants, and mutant of the regenerated plants are also included within the scope of the invention, provided that these parts compromise the introduced nucleic acid sequences.

A preferred embodiment is a transgenic plant that is homozygous for the added exogenous nucleic acid molecule; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non-transgenic plant are also contemplated.

The particular non-hydrolytic CBP encoding sequence that is introduced can be chosen based on the chitin composition of the pathogen to which it is desired to improve resistance. Approaches for identifying appropriate non-hydrolytic CBPs are discussed elsewhere herein.

Alternatively, the present invention relates to methods of modulating the level of non-hydrolytic CBP in a plant by a) introducing an expression cassette containing a polynucleotide encoding a non-hydrolytic CBP, b) culturing the plant cell under plant cell growing conditions, and c) including expression of the polynucleotide for a time sufficient to modulate the level of non-hydrolytic CBP in the plant.

The method can also be viewed as a method of improving the resistance of a plant to a chitin containing pathogen by a) introducing an expression cassette containing a polynucleotide encoding a non-hydrolytic CBP, b) culturing the plant cell under plant cell growing conditions, and c) inducing expression of the polynucleotide for a time sufficient to modulate the level of non-hydrolytic CBP in the plant.

Pesticide use is now in general criticised as a result of increased environment and health awareness. There is therefore pressure to pursue alternative strategies in pest management. Insect viruses such as baculovirus can also be used a biological pest control systems, in view of the fact that they are able to kill specific insect pests and as such they thus represent as attractive alternative to the use of pesticides as biological pest control systems. These insect viruses are excellent candidates for specifies-specific, narrow spectrum insecticidal applications. Baculoviruses in particular have been shown to have no negative impacts on plants, mammals, birds, fish, or even on non-target insects.

It would be of interest to increase or enhance the infectiousness of insect viruses and one possible way of doing this would be to improve or enhance the ability of such viruses to degrade chitin. The genome of at least some insect viruses contain chitinase genes and genes encoding family 33 non-hydrolytic CBPs (see Table 1) and chitinase activity has been associated with insect virus infectivity. The observation that non-hydrolytic CBPs have a function which is to weaken the structure of chitin and hence to enhance the degradation of chitin thus provides a means for improving the ability of such viruses to weaken or degrade chitin, and a means to enhance the infectivity of such viruses.

The invention thus further provides a recombinant insect virus comprising a nucleic acid molecule that encodes an exogenous non-hydrolytic CBP, wherein said non-hydrolytic CBP is as defined herein.

As used herein "recombinant" includes reference to a virus that has been modified by the introduction of a heterologous or exogenous nucleic acid. Thus, for example, recombinant viruses express genes that are not found in identical form within the native (non-recombinant) form of the virus or express native genes as a result of deliberate human intervention that are otherwise abnormally expressed, under-expressed or not expressed at all. The term "recombinant" as used here does not encompass the alteration of the virus by naturally occurring events (e.g., spontaneous mutation, natural transformation/transduction/transposition) such as those occurring without deliberate human intervention.

The nucleic acid molecule that encodes the exogenous non-hydrolytic CBP can be placed under the control of appropriate promoters that are known in the art for expression in this biological context. Such promoters may be e.g. inducible or constitutive.

By "exogenous" non-hydrolytic CBP it is meant a non-hydrolytic CBP that is not encoded by the genome of the naturally occurring insect virus, i.e. it originates from a different species, or it has been artificially synthesised. As discussed above, family 33 CBPs such as fusolin are found in insect viruses and the invention excludes naturally occurring viruses.

The nucleic acid molecule that contains the sequence encoding the non-hydrolytic CBP is thus introduced into the insect virus using standard techniques that are well known in the art. The resultant recombinant virus may then also be selected and cultured according to methods that are known in the art.

Alternatively, the invention provides a recombinant insect virus that expresses a naturally occurring non-hydrolytic CBP, under the control of an exogenous promoter, so as to enhance or improve the expression thereof, or to change the expression profile of the protein. By "exogenous" promoter it is meant a promoter that does not normally control the expression of the non-hydrolytic CBP. It may be an insect virus promoter but it is considered to be exogenous if it is not found in its normal context in the recombinant insect virus.

The person skilled in the art can make the appropriate choice of virus for the particular pest or insect, in view of the fact that these viruses are in general host specific.

Similarly, the choice of the non-hydrolytic CBP that is introduced can be make based on the composition of the chitin substrate in the insect that is to be infected.

The invention thus provides a method of increasing the infectivity of an insect virus comprising introducing a nucleic acid molecule that encodes an exogenous non-hydrolytic CBP into the genome of said insect virus.

By improved infectivity it is meant that the insect virus infects its host more efficiently or at lower concentrations of virus than a wild type or unmodified virus does.

In addition to introducing an exogenous nucleic acid sequence encoding a non-hydrolytic CBP into the recombinant virus, it is also possible to introduce a sequence encoding a chitin hydrolytic enzyme such as a chitinase.

The invention further provides a composition comprising a recombinant insect virus comprising a nucleic acid molecule that encodes an exogenous non-hydrolytic CBP together with an appropriate carrier or diluent, or a recombinant insect virus that comprises an non-hydrolytic CBP under the control of an exogenous promoter.

Use of such recombinant insect viruses or compositions in past control is also provided, as in a method of treating a plant or animal comprising administering to said plant or animal an effective amount of a composition comprising a recombinant insect virus comprising a nucleic acid molecule that encodes an exogenous non-hydrolytic CBP together with an appropriate carrier or diluent.

As the present invention provides the first demonstration of the chitin degradation enhancing properties of non-hydrolytic CBPs as defined herein, and assays in which this activity can be assessed and measured, it can be see that the methods and assays of the present invention can be used to identify residues of non-hydrolytic CBPs which are important for the function in enhancing chitin degradation.

Thus, a yet further aspect of the invention provides a method for identifying residues in a non-hydrolytic CBP as defined herein which are important for enabling an enhancement of chitin degradation or for weakening chitin, said method comprising the steps of:

(i) mutating or otherwise altering one or more amino acid residues in the non-hydrolytic CBP, and
(ii) testing the effect of the mutations or alterations on the property of enhancing chitin degradation or weakening chitin.

In such a method, step (ii) can be performed by assessing the ability of the mutated or otherwise altered non-hydrolytic CBP to enhance the degradation of chitin or weaken chitin, e.g. by using the methods and assays as described elsewhere herein. A comparison of the ability of the mutated or otherwise altered non-hydrolytic CBP to enhance the degradation of chitin or weaken chitin can then be made relative to the non-mutated or otherwise altered non-hydrolytic CBP. The properties of the mutated or otherwise altered non-hydrolytic CBP can thus be compared directly to the wild type, or parent sequence from which mutated or otherwise altered non-hydrolytic CBP is derived.

In such methods, the mutations may have no effect on the enhancement of degradation or may improve or reduce or inhibit the effect on enhancement of degradation. The residues which when mutated have a positive or negative effect on the enhancement of chitin degradation or for weakening chitin are then identified as being important for function. Depending on the proposed use for the non-hydrolytic CBPs such residues are either targets for further mutation (see below) or are identified as residues which should be retained in an unmodified form in order to preserve the important functional property of enhancing chitin degradation.

Alternatively viewed therefore, this provides a method for generating a non-hydrolytic CBP with improved or increased ability to enhance the degradation of chitin or for weakening chitin.

The present invention further provides a method of identifying, developing or producing other non-hydrolytic CBPs which can enhance chitin degradation or can weaken chitin, or variants thereof which have the ability to act on other substrates/polymers, said method comprising the steps of:

(i) obtaining or otherwise providing a non-hydrolytic CBP as defined herein,
(ii) mutating or otherwise altering one or more amino acid residues in the non-hydrolytic CBP,
(iii) assessing the ability of said mutated or altered non-hydrolytic CBP to degrade or to enhance the degradation of the substrate of interest or weaken the substrate of interest,
(iv) identifying mutated or altered non-hydrolytic CBPs which display the desired properties.

Appropriate substrates for use in the above methods could be any substrate or polymer of interest, in particular any carbohydrate based structure or polymer. Specific and preferred examples include any of the forms of chitin described elsewhere herein (in particular chitin copolymers), cellulose and lignocellulose. As indicated above, such methods can be used to identify, develop or produce binding proteins which weaken a different substrate or enhance the degradation of a different substrate to the starting non-hydrolytic CBP, e.g. a different form of chitin or copolymer or a different substrate such as cellulose or lignocellulose.

The non-hydrolytic CBP used in these methods has the properties as defined elsewhere herein and may be a newly identified non-hydrolytic CBP or may be a known molecule whose properties of enhancement of chitin degradation or weakening of chitin have only become known by use of the methods and assays of the invention as defined elsewhere herein.

If it is the aim of these methods to target a new or different substrate from the one that the starting non-hydrolytic CBP acts on, then preferred residues for mutation or alteration are those which have been identified as being important for binding to chitin and preferably those which have been identified as being important or essential for the enhancement of chitin degradation or weakening of chitin. Preferred residues for mutation are thus those which are exposed at the surface of the binding proteins and in particular those present on the surface which binds to the substrate (the binding surface). In the case of non-hydrolytic CBPs as described herein, preferred residues for mutation in the binding surface are residues which form part of the polar surface patch which is involved in substrate binding (as opposed to a binding surface dominated by aromatic residues such as those found in cellulose binding domains/modules). Preferred residues are thus polar residues (as opposed to aromatic residues) which are capable of forming specific polar interactions, e.g. hydrogen bonds, with the substrate.

Figure 2:
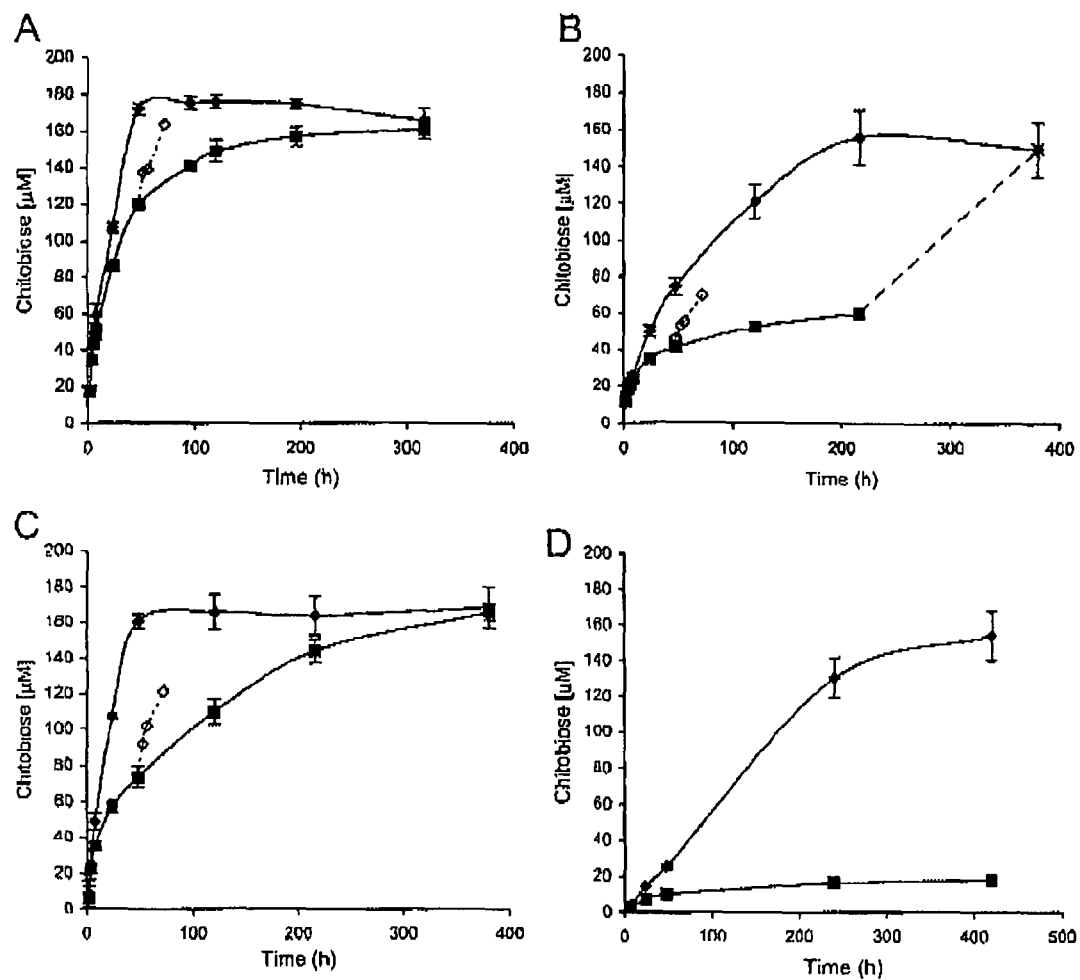
Figure 7:
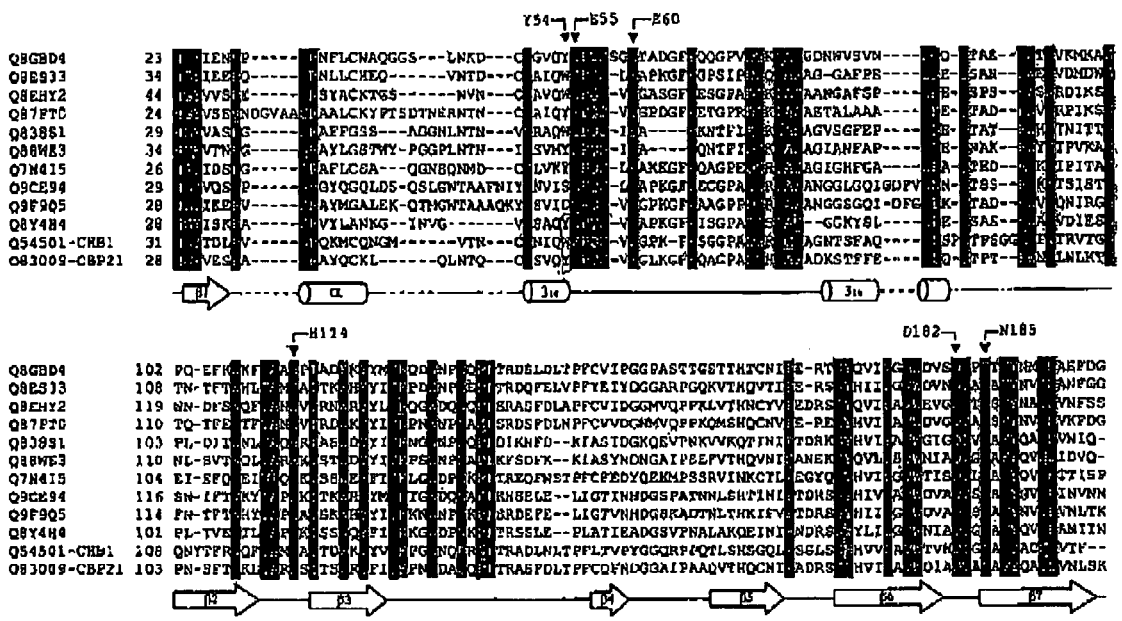

In the case of non-hydrolytic CBP21 particularly preferred residues for mutation are at amino acid positions 54, 55, 60, 114, 182 and 185 (i.e. Y54, E55, E60, H114, D182 and N185) which have been shown to be important in the binding of CBP21 to β chitin. Especially preferred residues for mutation are those which have been shown to be important in the ability of CBP21 to enhance chitin degradation or weaken chitin, i.e. at amino acid positions 54, 55, 60, 114 and 182 (i.e. Y54, E55, E60, H114 and D182). In the case of other non-hydrolytic CBPs, preferred residues for mutation are the corresponding residues to those given above for CBP21. Methods for determining the corresponding residues in other non-hydrolytic CBPs are readily available to a person skilled in the art and conveniently will involve sequence alignments using publicly available database as described elsewhere herein and databases such as ClustalX and T-COFFEE, which will allow the identification of corresponding residues. Examples of alignments of other bacterial CBPs with CBP21 and disclosure of corresponding residues and the amino acid position thereof are shown in FIG. 7 (FIG. 2 of Vaaje-Kolstad et al 2005, supra). As more structures of non-hydrolytic CBP-like proteins become available, structural comparisons and structure-based sequence alignments (methods which are readily available to the person skilled in the art), will be of increased utility in the process of identifying mutation targets in the binding surface area. A particularly preferred residue for mutation is the Y54 residue in CBP21 and its corresponding residue in CBP homologues (see for example the corresponding residues shown in FIG. 7). The corresponding residue in CHB1 is Trp57.

Mutation at the residues which are important for the function of enhancing chitin degradation or weakening chitin are likely to result in a modified function, for example an ability to bind to an preferably enhance degradation of or weaken another type of chitin from the original CBP or a different substrate such as those outlined above.

The present invention further provides a method of identifying non hydrolytic CBP homologues or related proteins from other organisms or the same organism, said method comprising the steps of:
 (i) obtaining or otherwise providing one or more molecules of interest which are candidate homologue or related protein molecules, and
 (ii) testing or screening to assess whether said molecule of interest is a non-hydrolytic CBP which enhances chitin degradation or weakens chitin as defined above, or is a related protein with activities toward other substrates.

Appropriate substrates for use in the above methods could be any substrate or polymer of interest, in particular any carbohydrate based structure or polymer. Specific and preferred examples include any of the forms of chitin described elsewhere herein (in particular chitin copolymers), cellulose and lignocellulose. As indicated above, such methods can be used to identify homologues or related proteins which enhance the degradation of the same substrate to the known or characterised non-hydrolytic CBP or a different substrate to the known or characterised non-hydrolytic CBP, e.g. a different form of chitin or copolymer or a different substrate such as cellulose or lignocellulose.

The molecules of interest used in step (i) of the method could be single molecules, or could be a library of molecules derived or cloned from one or more species of organism. For example, the molecules could be a library of genes which have been cloned and expressed for testing in accordance with the above method. Any appropriate library of molecules may be used, e.g. cDNA library, genomic fragments, etc. In addition, the library of molecules could represent a library of non-hydrolytic CBP variants, produced e.g. by mutagenesis, which are to be tested for their activities on various substrates.

Although the initial library of molecules may be in the form of nucleic acid sequences, for the test or screening step it is required that the molecules are in the form of proteins (i.e. the nucleic acid molecules need to be expressed). Appropriate methods of expression are well known and described in the art and an appropriate one can be selected. The molecules to be expressed can then be cloned into appropriate expression vectors based on the host cell which is to be used. Preferably for example the molecules to be tested can be cloned into appropriate vectors for expression and preferably secretion from bacterial hosts such as E. coli. Equally however, eukaryotic host cells could be used.

The molecules used in step (i) of the method could be identified or obtained in any appropriate way, e.g. by genome mining, sequence comparison searches, e.g. using sequence databases, etc.

Preferably the bacterial host (or other host) will have some (but preferably a limited) ability to degrade the substrate of interest alone. Optionally the bacterial host can also be engineered to express and secrete an appropriate substrate degrading enzyme, e.g. an appropriate chitinase or cellulase (depending on the substrate of interest). One could then transform these bacteria with a library of protein molecules of interest, e.g. a library of CBP variants, and plate these bacteria on substrate containing plates. An increased halo size would then slow the presence of an effective binding protein.

Alternatively, any appropriate reaction vessel can be used to test the protein molecules. If a library of molecules are to be tested then conveniently each individual protein molecule to be tested is present in an individual reaction vessel, e.g. an assay tube or well. The assays for non-hydrolytic CBPs or related proteins which can enhance the degradation of chitin (or other substrates) can be carried out in such reaction vessels in accordance with the methods of the invention as described herein. For example a certain substrate can be brought into contact with CBPs or related proteins under test (which can either be purified or present in culture supernatants), optionally in combination with an appropriate hydrolytic enzyme, e.g. a chitinase or a cellulase. The degree of substrate degradation can then be monitored, for example by measuring the turbidity in the vessel. Preferred conditions for carrying out these methods to assess substrate degradation are as described elsewhere herein.

In an alternative to the method described above, it would be possible to use a microorganism that can utilize GlcNAc2 as a source of energy, a slow working chitinase and pure crystalline chitin in combination with the various CBPs to be tested. After suitable incubation the mixtures can be analysed for any increase in cell density (turbidity). If the CBP variant is effective, cell growth will be observed. If not, the cells won't grow since the chitinase alone will not produce GlcNAc2 sufficiently rapidly.

Thus, methods of testing or assessing the abilities as described in the above methods can be carried out in accordance with the methods of the invention, in the presence or absence of appropriate chitin hydrolase, e.g. chitinases, as described elsewhere herein. If the methods are designed to identify molecules which are reactive to a non-chitin substrate then appropriate enzymes which facilitate the degradation of these substrates (e.g. appropriate hydrolytic enzymes) can be added in order to assess whether the identified molecule has an effect on enhancing the degradation. For example in the case of cellulose, appropriate cellulases can be added.

In any of the above methods where mutation steps are involved, then any appropriate methods of mutagenesis could be used, for example site directed mutagenesis, random mutagenesis or directed evolution, e.g. random mutagenesis followed by screening. Such techniques are well known to a person skilled in the art.

Substrate binding proteins and proteins which degrade or enhance the degradation of substrate that are identified, developed or produced by any of the above methods and the use thereof to enhance the degradation of substrate form yet further aspects of the invention. These proteins can optionally be manufactured and optionally formulated into compositions for various uses.

In all the above described embodiments, the non-hydrolytic CBPs, and preferred non-hydrolytic CBPs for use in these methods are as defined elsewhere herein.

This invention will now be described in more detail in the following non-limiting Examples with reference to the drawings in which:

FIG. 1 shows scanning electron micrographs of β-chitin particles. The figure shows representative pictures of structures observed in the absence or presence of CBP21. Control particles (no CBP21 added) are shown in panels A and B (400× magnification) with close ups (5000× magnification) of the respective particles shown in panel E and F, respectively. Particles incubated with CBP21 are shown in panels C and D, with close ups (5000× magnification) shown in panels G and H, respectively. The black frame drawn on the 400× magnified images indicate the area targeted for the picture taken at 5000× magnification. The scale bars in panels A-D and E-H represent 50 and 5 μm, respectively.

FIG. 2 shows degradation of β-chitin in the absence or presence of CBP21. Reaction mixtures contained 0.1 mg/ml β-chitin, 0.2 μM enzyme and 5 μM CBP21, added at t=0, unless stated otherwise. The lines connecting the points are drawn for illustration purposes only. (A) ChiA (squares), ChiA+CBP21 (closed diamonds) or ChiA+CBP21 added at t=48 h (open diamonds). (B) ChiB (squares), ChiB+CBP21 (closed diamonds), ChiB+CBP21 added at t=48 h (open diamonds) or ChiB+CBP21 added at t=216 h (squares connected by a dashed line; see text for details). C) ChiC (squares), ChiC+CBP21 (closed diamonds) or ChiC+CBP21 added at t=48 h (open diamonds) and D) 0.3 μM ChiG (squares) or 0.3 μM ChiG+5 μM CBP21 (diamonds).

Figure 3:
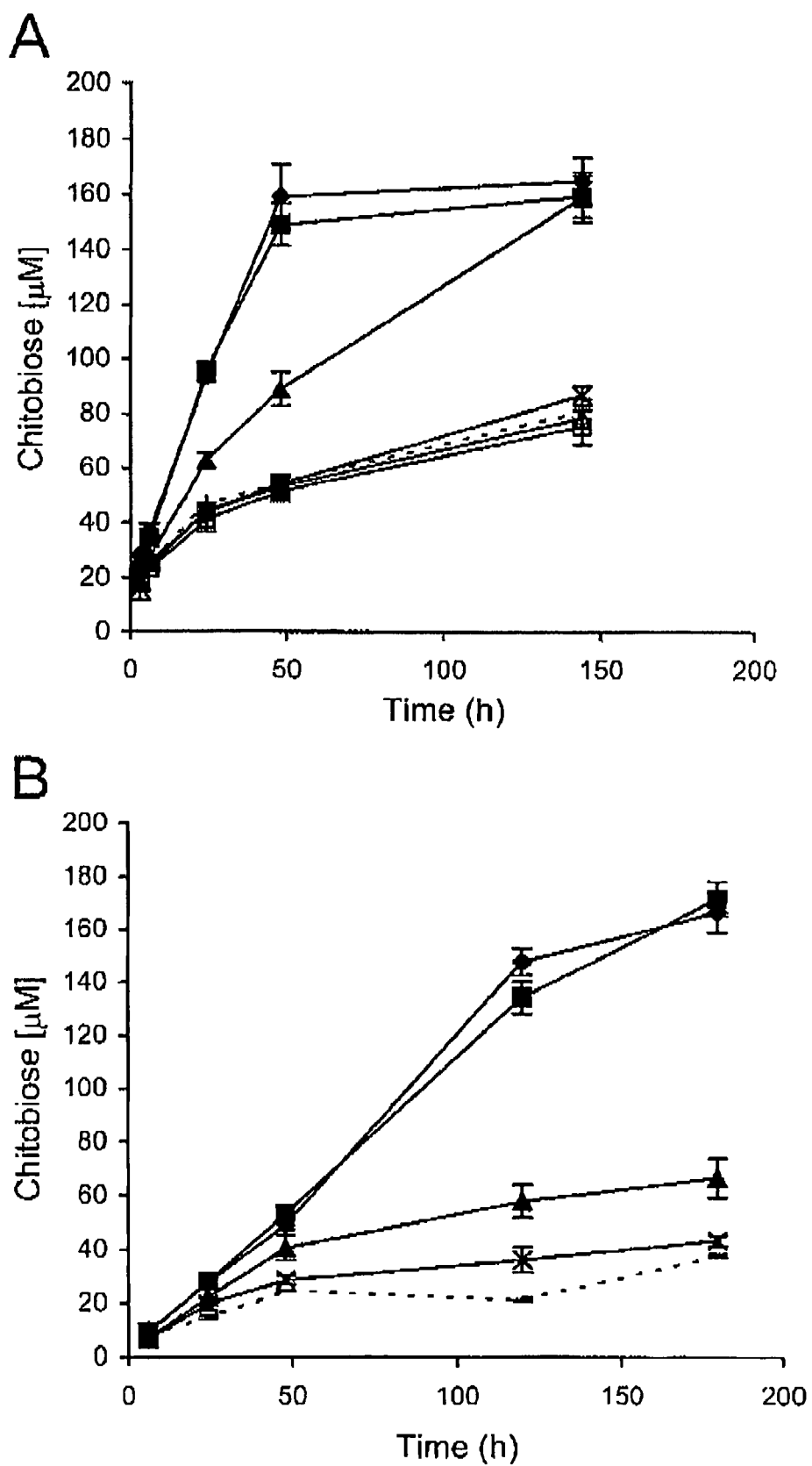

FIG. 3 shows dose response effects for ChiC. Reaction mixtures contained 0.1 mg/ml β-chitin, 50 nM (A) or 5 nM (B) Chic and 500 (diamonds), 50 (squares), 5 (triangles), 0.5 (crosses), 0.05 (hollow squares), 0.005 (hollow triangles) or 0 nM CBP21 (dotted line).

Figure 4:
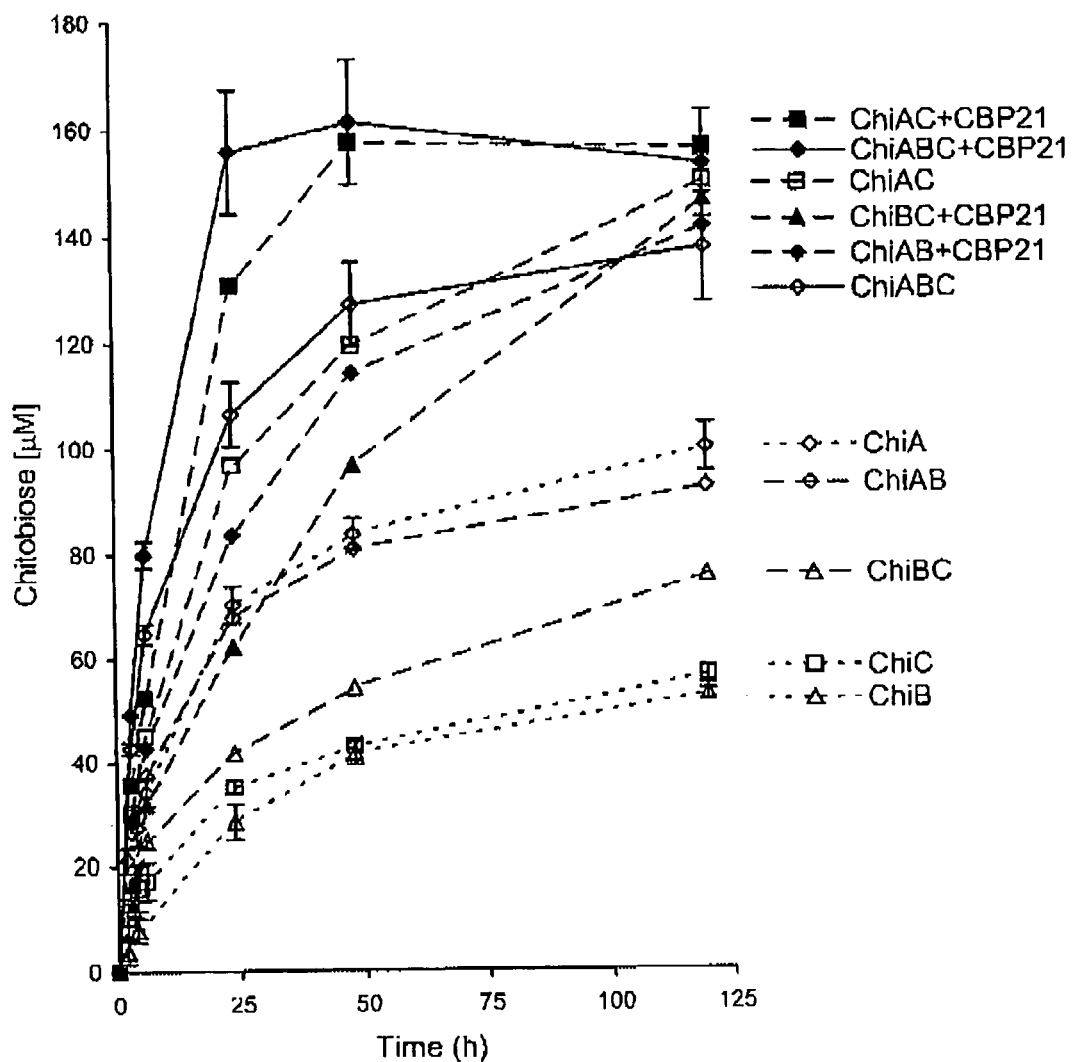

FIG. 4 shows synergistic effects in the degradation of β-chitin. The curves shows progress in degradation of β-chitin with various combinations of chitinases (as indicated by combinations of the letters A, B and C) and CBP21. The total enzyme concentration was always 50 nM, meaning that the reactions mixtures with one, two or three chitinases contained 50, 25 or 16.7 nM of each enzyme, respectively. The CBP21 concentration was 50 nM. For illustration purposes, the points are connected by dotted lines (single enzyme reactions), dashed lines (two-enzyme reactions) or solid lines (three-enzyme reactions). The effect of CBP21 may be evaluated by comparing curves with solid symbols (with CBP21) with curves with corresponding hollows symbols (same enzyme combination, no CBP21).

Figure 5:
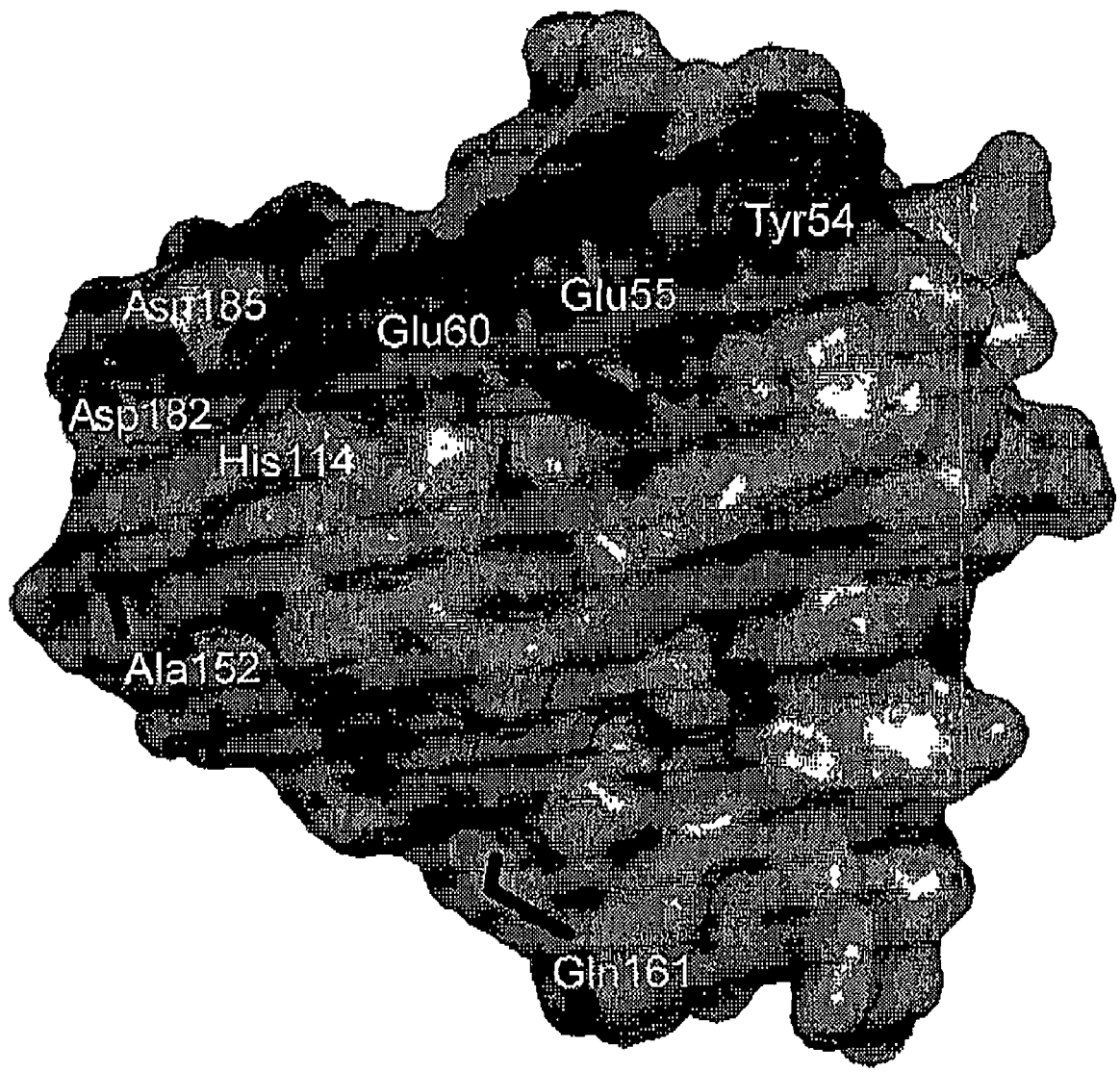

FIG. 5 shows the structure of CBP21. The side chains of all mutated residues are shown as sticks. Note that Ala152 and Gln161 were not expected to be involved in chitin binding.

Figure 6:
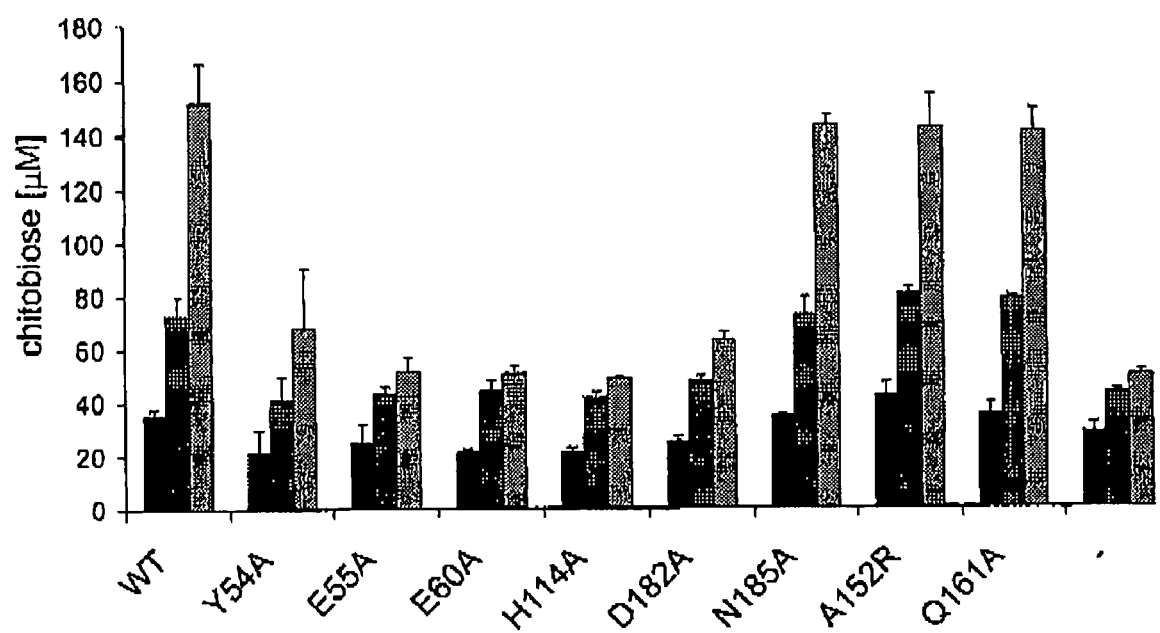

FIG. 6 shows the degradation of β-chitin by ChiC in the presence of CBP21 mutants. Degradation of 0.1 mg/ml β-chitin with 50 nM ChiC in the presence of 50 nM CBP21 wild-type, Y54A, E55A, E60A, H114A, D182A, N185A, A152R or no CBP21 (indicated by a hyphen). Total product release is shown as black bars (24 h), grey bars (48 h) and light grey bars (120 h).

FIG. 7 shows multiple alignment of bacterial CBPs (Q8GBD4 [SEQ ID NO: 2], *Yersinia enterocolitica*; Q8ES33 [SEQ ID NO: 3], *Oceanobacillus iheyensis*; Q8EHY2 [SEQ ID NO: 4], *Shewanella oneidensis*; Q87FT0 [SEQ ID NO: 5], *Vibrio parahaemolyticus*; Q838S1 [SEQ ID NO: 6], *Enterococcus feacalis*; Q88WE3 [SEQ ID NO: 7], *Lactobacillus plantarum*; Q7N415 [SEQ ID NO: 8], *Photorhabdus luminescens* (subsp. *laumondii*); Q9CE94 [SEQ ID NO: 9], *Lactococcus lactis* (subsp. *lactis*); Q9F9Q5* [SEQ ID NO: 10], *Bacllus amyloliquefaciens*; Q8Y4H4 [SEQ ID NO: 11], *Listeria monocytogenes*; Q54501* [SEQ ID NO: 12], *Streptomyces olivaceoviridis* (CHB1); O83009* [SEQ ID NO: 13], *Serratia marcescens* (CBP21)). CBPs marked with asterisks have been shown to bind chitin. The secondary structure elements of CBP21 are also shown and labelled. Arrows with residue numbers indicate residues mutated in Vaaje-Kolstad et al. (2005) JBC 280(12), 11313-11319. The multiple alignment was created with ClustalX and edited with T-COFFEE.

EXAMPLES

Example 1

Scanning Electron Microscopy of β-Chitin Fragments

A 0.1 mg/ml β-chitin (France Chitin, Marseille) suspension in 50 μM phosphate buffer, pH 6.3 was pre-incubated for 48 hours at 37° C. in Eppendorf tubes with either 0.1 mg/ml BSA or 0.1 mg/ml BSA and 0.1 mg/ml CBP21, applied onto an object glass (10 mm; 25 μl drops), and dried at 37° C. in order to fix the sample. CBP21 was produced as described in Vaaje Kolstad et al. 2005, JBC 280 (12) 11313-9 which is incorporated herein by reference. The object glasses containing the samples were glued onto SEM aluminium studs with carbon tape and sputter-coated with gold-palladium. Scanning was performed in a JEOL JSM 6400 scanning electron microscope at 5 kV.

The edges and surfaces of the untreated particles are discrete in shape, with smooth surfaces (FIG. 1. panels A, B, E and F). In contrast, the edges and surfaces of the CBP21-treated particles showed an amorphous and porous character (FIG. 1, panels C and G), along with areas of disassembled chitin fibrils (FIG. 1, panels D and H).

Example 2

Degradation of β-Chitin with Different Chitinases

ChiA, ChiB and ChiC (Synstad et al., Genbank accession number AJ630582) from *Serratia marcescens* BJL200 were overexpressed in *E. coli* and purified from periplasmic extracts using a two-step procedure. The first step consisted of standard ion-exchange chromatography using Q-Sepharose Fast Flow (Amersham Pharmacia Biotech AB) at pH 9.4 to separate the chitinases from the majority of proteins in the periplasmic extracts. The second step consisted of hydrophobic interaction chromatography using a phenyl superpose 5/5 column (Amersham Pharmacia Biotech AB, Uppsala, Sweden), as described elsewhere (Brurberg et al. (1996) Microbiology-UK 142, 1581-1589). His-tagged ChiG from *Streptomyces coelicolor* A3(2) (Genbank AB016103) was cloned behind a T7 promoter into the pETM11 (Günter Stier, EMBL Heidelberg, Germany) expression vector. The protein was produced in isopropyl-β-D-thiogalactopyranosid (IPTG) induced *E. coli* BL21 DE3 cells; cells were lysed by sonication an the protein was purified using a nickel column (5×2 cm, Qiagen), under standard conditions. All proteins were dialysed into 20 mM Tris-HCl, pH 8.0 before use and stored at 4° C.

Determination of chitinolytic activity was done using β-chitin from squid pen (France Chitin, Marseille), α-chitin isolated from shrimp shells (Hov-Bio, Tromsø, Norway) or crab shells (Sigma) or microparticulate β-chitin (Seikagaku Corp., Japan) as substrate. Standard reaction mixtures contained varying concentrations of chitinase and CBP21, 0.1 mg/ml purified BSA, 0.1 mg/ml chitin powder (unless stated otherwise), in 50 mM sodium phosphate buffer, pH 6.3. Reaction mixtures were incubated at 37° C. for up to two weeks. No agitation was used since the insoluble substrate easily adheres to the dry inner walls of the Eppendorf tubes, which would affect the substrate concentration. At time points ranging from 2 hours to 400 hours, 60 µl of the reaction mixture was transferred to an Eppendorf tube containing 60 µl 70% acetonitrile, to stop the reaction. Before taking samples, reaction mixtures were resuspended by gentle pipetting in order to leave the chitin concentration unaltered. All reactions were run in triplicate and all samples were stored at −20° C. until further analysis.

Samples were analysed by isocratic high performance liquid chromatography (HPLC) using an Amide-80 column (Tosoh Bioscience, Montgomeryville, Pa., USA), coupled to a Gilson Unipoint HPLC system (Gilson). The liquid phase consisted of 70% acetonitrile, with a flow rate of 0.7 ml/min, 20 µl samples were injected using a Gilson 123 autoinjector. Eluted oligosaccharides were monitored by recording absorption at 210 nm. Chromatograms were collected and analysed using the Gilson Unipoint software (Gilson). Since in all cases (GlcNAc)$_2$ represented more than 95% of the total amount of degradation products on a molar basis, only (GlcNac)$_2$ peaks were subject for data analysis and used for quantification of the extent of chitin degradation. A standard solution containing 0.25 mM (GlcNAc)$_2$ was analyzed at the start, in the middle and at the end of each series of samples, and the resulting average value (displaying standard deviations of less than 3%) was used for calibration.

Degradation of β-chitin with the family 18 chitinases ChiA, ChiB or ChiC showed biphasic kinetics, with an initial fast linear phase, followed by a slower, hyperbolic phase (FIG. 2, panels A, B and C). Initial degradation rates were determined by linear regression, whereas the hyperbolic second phase only allowed endpoint analysis as a rate descriptor (Table 2). In the absence of CBP21 ChiA and ChiC had similar activities toward chitin, both in terms of initial rate and the time needed to fully degrade the substrate ($t_{full}$), whereas ChiB displayed a ~3-fold slower initial rate and never managed to fully digest the substrate (FIG. 2, Table 2). The addition of CBP21 had only minor effects on the initial rates but large effects on the slower second phase (that is, on $t_{full}$). For ChiA and ChiC $t_{full}$ decreased approximately 7-fold, while, for ChiB, addition of CBP21 led to complete degradation of the substrate, albeit still at a slower rate than in the case of ChiA and ChiC (Table 2).

TABLE 2

Initial rates (calculated for the first four timepoints: 2, 4, 6 and 8 hours) and reaction end points ($t_{full}$) for the degradation of β-chitin with 0.2 µM ChiA, ChiB or ChiC, in the absence or presence of CBP21.

| Chitinase | Initial rate [µM (GlcNAc)$_2$/h] | | Endpoint ($t_{full}$) (h) | |
|---|---|---|---|---|
| | −CBP21 | +CBP21 | −CBP21 | +CBP21 |
| ChiA | 2.7 (0.95) | 3.4 (0.98) | ~360 | ~48 |
| ChiB | 0.9 (0.98) | 1.3 (0.99) | n.d. | ~200 |
| ChiC | 2.3 (0.93) | 3.3 (0.99) | ~360 | ~48 |

The R-square values from the linear regression analyses are indicated in brackets.
The data are derived from the curves shown in FIG. 2.
N.d.: "not determined".

In order to verify that the enzymes remained active during the reactions, a series of experiments were carried out, in which CBP21 was added after 48 hours pre-incubation with the chitinases. FIG. 2 shows that addition of CBP21 increase reaction rates to levels comparable to those observed in reactions where the CBP21 was present from t=0. In an additional control experiment with ChiB, CBP21 was added after 216 hours, which led to full degradation of the substrate (FIG. 2, panel B). Control reactions containing CBP21 without enzyme did not yield detectable amounts of soluble chitooligosaccharides. Taken together, these results demonstrate that CBP21 facilitates the degradation of β-chitin by family 18 chitinase in a non-enzymatic manner.

To investigate whether the effects of CBP21 on the efficiency of family 18 chitinases from *S. marcescens* were due to specific enzyme-CBP21 interactions, we also conducted experiments with ChiG, a family 19 chitinase from *Streptomyces coelicolor*. The results (FIG. 2, panel D) show that CBP21 increased ChiG efficiency, suggesting that CBP21 has a general effect on substrate availability and does not act through specific interactions with particular enzymes.

Dose-response studies of the effect of CBP21 on ChiC efficiency showed that ChiC displays maximum degradation rates of CBP21 concentrations ≧50 nM, regardless of the enzyme concentration (FIG. 3). Thus, the beneficial effects of CBP21 does not seem to be caused by a stoichiometric interaction with the enzyme.

Example 3

β-Chitin Degradation Using Combinations of ChiA, -B, -C and CBP21

It is generally assumed that ChiA and ChiB are exochitinases, while ChiC is an endochitinase and synergistic effects between these enzymes have been observed in studies with colloidal chitin and α-chitin. In agreement with previous experiments, FIG. 4 shows that the three *S. marcescens* chitinases are synergistically on β-chitin too. In all cases, CBP21 increased the degradation efficiency. The highest efficiency was obtained when combining all three enzymes in the presence of CBP21.

Example 4

Hydrolysis of β-Chitin with ChiC in the Presence of CBP21 Mutants

CBP21 mutants were produced as described in Vaaje Kolstad et al. 2005 JBC 280(12) 11313-9. Combination of the structure of CBP21 with a multiple sequence alignment of bacterial CBPs has previously revealed conserved surface residues, whose mutation to alanine decreased chitin affinity 2- to 8-fold. These mutants, as well as two control CBP21 variants with wild type binding characteristics (A152R and Q161A), were used in hydrolysis studies with ChiC. Experiments with a CBP21 concentration of 50 nM, which give maximum effects on ChiC efficiency in the case of wild type CBP21 (FIG. 3), showed that CBP21 mutants Y54A, E55A, E60A, H114A and D182A had lost their functionality (FIG. 6). The deleterious effects of the Y54A, E55A and H114A mutations on CBP21 function were only slightly negated by increasing the CBP21 concentration as much as 100-fold (results not shown, E60A and D182A were not tested).

Example 5

Hydrolysis of Other Chitin Forms

The three family 18 chitinases from *Serratia marcescens* can degrade several chitin forms for which CBP21 has low affinity, for example α-chitin from crab shells and shrimp shells. Experiments similar to the ones described above showed that addition of CBP21 at concentrations up to as high as 5 μM did not affect of the efficiency of ChiA, ChiB and ChiC towards these substrates (results not shown).

The invention claimed is:

1. A method of enhancing chitin degradation comprising the steps:
   (i) adding simultaneously or sequentially in either order a chitin binding protein (CBP) and a chitin hydrolase to a chitin substrate to produce a chitin degradation mixture, and
   (ii) incubating said mixture for at least 2 hours at a temperature appropriate for enhancing chitin degradation, wherein said CBP comprises
   (a) CBP21, as set forth in SEQ ID NO:1 or amino acids 28-197 of SEQ ID NO: 1, or
   (b) a functional variant thereof which retains one or more of: a tyrosine residue at position 54, a glutamic acid residue at position 55, a glutamic acid residue at position 60, a histidine residue at position 114, an aspartic acid residue at position 182 and an asparagine residue at position 185, wherein the positions are according to the numbering of SEQ ID NO:1,
   wherein the CBP enhances chitin degradation, and
   wherein said CBP is synthetic or recombinant or said CBP is isolated, extracted, purified, or concentrated from a microorganism which naturally produces said CBP or from a supernatant into which said microorganism has secreted said CBP.

2. The method of claim 1 wherein said chitin is a chitin, β chitin, γ chitin, amorphous chitin, colloidal chitin, chitin forms in which part of the N-acetylglucosamine sugars are deacetylated, chitosan, or a copolymer of chitin.

3. The method of claim 1 which method comprises the steps of:
   (i) contacting said CBP and chitin under appropriate conditions so as to allow said CBP and chitin to interact or bind to each other, and
   (ii) incubating under appropriate conditions to allow enhancement of degradation to occur.

4. The method of claim 3 wherein the incubation step is carried out for 12 hours or more.

5. The method of claim 3 wherein said method is carried out at an appropriate pH.

6. The method of claim 3 wherein steps (i) and/or (ii) are carried out at pH 6 to 6.5.

7. The method of claim 3 wherein said method is carried out without agitation.

8. The method of claim 1 wherein said functional variants display at least 70, 80, 85, 90, 91, 92, 93, 94, 95, 96, 97, 98 or 99% sequence similarity or identity with SEQ ID NO:1 or amino acids 28 to 197 of SEQ ID NO:1 at the amino acid level.

9. The method of claim 1 wherein said chitin hydrolase is a chitinase enzyme.

10. The method of claim 9 wherein said chitinase enzyme is one or more of ChiA, ChiB, ChiC and/or ChiG.

11. The method of claim 1, wherein said functional variants retain all of a tyrosine residue at position 54, a glutamic acid residue at position 55, a glutamic acid residue at position 60, a histidine residue at position 114, an aspartic acid residue at position 182 and an asparagine residue at position 185, said numberings being according to SEQ ID NO: 1.

12. The method of claim 1 wherein said CBP is isolated, extracted, purified, or concentrated from a microorganism which naturally produces said CBP21 or from a supernatant into which said microorganism has secreted said CBP21.

13. The method of claim 12 which method comprises the steps of:
   (i) contacting said CBP and chitin under appropriate conditions so as to allow said CBP and chitin to interact or bind to each other, and
   (ii) incubating under appropriate conditions to allow enhancement of degradation to occur.

14. The method of claim 13 wherein the incubation step is carried out for 12 hours or more.

15. The method of claim 13 wherein the incubation step is carried out for 4 hours or more.

16. The method of claim 1 wherein the incubation step is carried out for 4 hours or more.

17. The method of claim 1 wherein the incubation step is carried out for 12 hours or more.

18. The method of claim 3 wherein the incubation step is carried out for 4 hours or more.

* * * * *

SEQUENCE LISTING

```
<160> NUMBER OF SEQ ID NOS: 13

<210> SEQ ID NO 1
<211> LENGTH: 197
<212> TYPE: PRT
<213> ORGANISM: Serratia marcescens

<400> SEQUENCE: 1

Met Asn Lys Thr Ser Arg Thr Leu Leu Ser Leu Gly Leu Leu Ser Ala
1               5                   10                  15

Ala Met Phe Gly Val Ser Gln Gln Ala Asn Ala His Gly Tyr Val Glu
            20                  25                  30

Ser Pro Ala Ser Arg Ala Tyr Gln Cys Lys Leu Gln Leu Asn Thr Gln
        35                  40                  45

Cys Gly Ser Val Gln Tyr Glu Pro Gln Ser Val Glu Gly Leu Lys Gly
    50                  55                  60

Phe Pro Gln Ala Gly Pro Ala Asp Gly His Ile Ala Ser Ala Asp Lys
65                  70                  75                  80

Ser Thr Phe Phe Glu Leu Asp Gln Gln Thr Pro Thr Arg Trp Asn Lys
                85                  90                  95

Leu Asn Leu Lys Thr Gly Pro Asn Ser Phe Thr Trp Lys Leu Thr Ala
            100                 105                 110

Arg His Ser Thr Thr Ser Trp Arg Tyr Phe Ile Thr Lys Pro Asn Trp
        115                 120                 125

Asp Ala Ser Gln Pro Leu Thr Arg Ala Ser Phe Asp Leu Thr Pro Phe
    130                 135                 140

Cys Gln Phe Asn Asp Gly Gly Ala Ile Pro Ala Ala Gln Val Thr His
145                 150                 155                 160

Gln Cys Asn Ile Pro Ala Asp Arg Ser Gly Ser His Val Ile Leu Ala
                165                 170                 175

Val Trp Asp Ile Ala Asp Thr Ala Asn Ala Phe Tyr Gln Ala Ile Asp
            180                 185                 190

Val Asn Leu Ser Lys
            195

<210> SEQ ID NO 2
<211> LENGTH: 173
```

```
<212> TYPE: PRT
<213> ORGANISM: Yersinia enterocolitica

<400> SEQUENCE: 2

His Gly Tyr Ile Glu Asn Pro Pro Ser Arg Asn Phe Leu Cys Asn Ala
1               5                   10                  15

Gln Gly Gly Ser Leu Asn Lys Asp Cys Gly Gly Val Gln Tyr Glu Pro
            20                  25                  30

Gln Ser Ser Gly Glu Thr Ala Asp Gly Phe Pro Gln Gln Gly Pro Val
        35                  40                  45

Asp Gly Lys Leu Ala Ser Gly Asp Asn Trp Val Ser Val Asn Leu Asn
50                  55                  60

Gln Gln Thr Ala Glu Arg Trp Thr Lys Val Lys Met Lys Ala Gly Pro
65                  70                  75                  80

Gln Glu Phe Lys Trp Lys Phe Thr Ala Ala His Pro Ile Ala Asp Phe
                85                  90                  95

Lys Tyr Tyr Met Thr Lys Gln Asp Trp Asn Pro Asn Gln Pro Leu Thr
            100                 105                 110

Arg Asp Ser Leu Asp Leu Thr Pro Phe Cys Val Ile Pro Gly Gly Pro
        115                 120                 125

Ala Ser Thr Thr Gly Ser Thr Thr His Thr Cys Asn Ile Pro Glu Arg
130                 135                 140

Thr Gly Tyr Gln Val Ile Tyr Gly Ala Trp Asp Val Ser Asp Thr Pro
145                 150                 155                 160

Gly Thr Phe Tyr Asn Met Ile Asp Ala Glu Phe Asp Gly
                165                 170

<210> SEQ ID NO 3
<211> LENGTH: 168
<212> TYPE: PRT
<213> ORGANISM: Oceanobacillus iheyensis

<400> SEQUENCE: 3

His Gly Tyr Ile Glu Glu Pro Gln Ser Arg Asn Leu Leu Cys His Glu
1               5                   10                  15

Gln Val Asn Thr Asp Cys Gly Ala Ile Gln Trp Glu Pro Gln Ser Leu
            20                  25                  30

Glu Ala Pro Lys Gly Phe Pro Gly Pro Ser Ile Pro Asp Gly Gln Ile
        35                  40                  45

Ala Ser Ala Gly Gly Ala Phe Pro Glu Leu Asp Glu Gln Ser Ala Asn
50                  55                  60

Arg Trp Glu Lys Val Asp Met Asp Trp Gly Thr Asn Thr Phe Thr Trp
65                  70                  75                  80

His Leu Thr Ala Met His Ala Thr Thr Lys Trp His Tyr Tyr Ile Thr
                85                  90                  95

Lys Pro Asp Trp Asn Pro Asn Glu Pro Leu Thr Arg Asp Gln Phe Glu
            100                 105                 110

Leu Val Pro Phe Tyr Glu Ile Tyr Asp Gly Gly Ala Arg Pro Gly Gln
        115                 120                 125

Lys Val Thr His Gln Val Thr Ile Pro Glu Arg Ser Gly Tyr His Ile
130                 135                 140

Ile Leu Gly Val Trp Asp Val Asn Asp Thr Ala Asn Ala Phe Tyr Asn
145                 150                 155                 160

Val Ile Asp Ala Asn Phe Gly Gly
                165
```

```
<210> SEQ ID NO 4
<211> LENGTH: 170
<212> TYPE: PRT
<213> ORGANISM: Shewanella oneidensis

<400> SEQUENCE: 4

His Gly Tyr Val Val Ser Pro Glu Ser Arg Ser Tyr Ala Cys Lys Thr
1               5                   10                  15

Gly Ser Asn Val Asn Cys Gly Ala Val Gln Trp Glu Pro Gln Ser Val
            20                  25                  30

Glu Gly Ala Ser Gly Phe Pro Glu Ser Gly Pro Ala Asp Gly Lys Ile
        35                  40                  45

Ala Ser Ala Ala Asn Gly Ala Phe Ser Pro Leu Asp Glu Gln Ser Pro
    50                  55                  60

Ser Arg Trp Ser Lys Arg Asp Ile Lys Ser Gly Trp Asn Asp Phe Ser
65                  70                  75                  80

Trp Gln Phe Thr Ala Asn His Val Thr Arg Asn Trp Arg Tyr Tyr Leu
                85                  90                  95

Thr Arg Gln Gly Trp Asp Gln Asn Gln Pro Leu Ser Arg Ala Ser Phe
            100                 105                 110

Asp Leu Ala Pro Phe Cys Val Ile Asp Gly Gly Met Val Gln Pro Pro
        115                 120                 125

Lys Leu Val Thr His Asn Cys Tyr Val Pro Glu Asp Arg Ser Gly Tyr
    130                 135                 140

Gln Val Ile Leu Ala Val Trp Glu Val Gly Asp Thr Thr Asn Ser Phe
145                 150                 155                 160

Tyr Asn Ala Ile Asp Val Asn Phe Ser Ser
                165                 170

<210> SEQ ID NO 5
<211> LENGTH: 180
<212> TYPE: PRT
<213> ORGANISM: Vibrio parahaemolyticus

<400> SEQUENCE: 5

His Gly Tyr Val Ser Glu Ser Asn Asp Gly Val Ala Ala Ser Arg Ala
1               5                   10                  15

Ala Leu Cys Lys Tyr Pro Thr Ser Asp Thr Asn Glu Arg Asn Thr Asn
            20                  25                  30

Cys Gly Ala Ile Gln Tyr Glu Pro Gln Ser Val Glu Gly Pro Asp Gly
        35                  40                  45

Phe Pro Glu Thr Gly Pro Arg Asp Gly Lys Ile Ala Ser Ala Glu Thr
    50                  55                  60

Ala Leu Ala Ala Ala Leu Asp Glu Gln Thr Ala Asp Arg Trp Val Lys
65                  70                  75                  80

Arg Pro Ile Lys Ser Gly Thr Gln Thr Phe Glu Trp Thr Phe Thr Ala
                85                  90                  95

Asn His Val Thr Arg Asp Trp Lys Tyr Tyr Ile Thr Lys Pro Asn Trp
            100                 105                 110

Asn Pro Asn Ala Ser Leu Ser Arg Asp Ser Phe Asp Leu Asn Pro Phe
        115                 120                 125

Cys Val Val Asp Gly Asn Met Val Gln Pro Pro Lys Gln Met Ser His
    130                 135                 140

Gln Cys Asn Val Pro Glu Arg Glu Gly Tyr His Val Ile Leu Ala Val
145                 150                 155                 160

Trp Asp Val Gly Asp Thr Ala Ala Ser Phe Tyr Asn Val Ile Asp Val
                165                 170                 175
```

```
Lys Phe Asp Gly
            180

<210> SEQ ID NO 6
<211> LENGTH: 166
<212> TYPE: PRT
<213> ORGANISM: Enterococcus faecalis

<400> SEQUENCE: 6

His Gly Tyr Val Ala Ser Pro Gly Ser Arg Ala Phe Phe Gly Ser Ser
1               5                   10                  15

Ala Gly Gly Asn Leu Asn Thr Asn Val Gly Arg Ala Gln Trp Glu Pro
            20                  25                  30

Gln Ser Ile Glu Ala Pro Lys Asn Thr Phe Ile Thr Gly Lys Leu Ala
        35                  40                  45

Ser Ala Gly Val Ser Gly Phe Glu Pro Leu Asp Glu Gln Thr Ala Thr
    50                  55                  60

Arg Trp His Lys Thr Asn Ile Thr Thr Gly Pro Leu Asp Ile Thr Trp
65                  70                  75                  80

Asn Leu Thr Ala Gln His Arg Thr Ala Ser Trp Asp Tyr Tyr Ile Thr
                85                  90                  95

Lys Asn Gly Trp Asn Pro Asn Gln Pro Leu Asp Ile Lys Asn Phe Asp
            100                 105                 110

Lys Ile Ala Ser Ile Asp Gly Lys Gln Glu Val Pro Asn Lys Val Val
        115                 120                 125

Lys Gln Thr Ile Asn Ile Pro Thr Asp Arg Lys Gly Tyr His Val Ile
    130                 135                 140

Tyr Ala Val Trp Gly Ile Gly Asp Thr Val Asn Ala Phe Tyr Gln Ala
145                 150                 155                 160

Ile Asp Val Asn Ile Gln
                165

<210> SEQ ID NO 7
<211> LENGTH: 168
<212> TYPE: PRT
<213> ORGANISM: Lactobacillus plantarum

<400> SEQUENCE: 7

His Gly Phe Val Thr Asn Pro Gly Gly Arg Ala Tyr Leu Gly Ser Thr
1               5                   10                  15

Trp Tyr Pro Gly Gly Pro Leu Asn Thr Asn Ile Gly Ser Val Met Tyr
            20                  25                  30

Glu Pro Gln Ser Ile Glu Ala Pro Gln Asn Thr Phe Ile Asp Gly Lys
        35                  40                  45

Ile Ala Ser Ala Gly Ile Ala Asn Phe Ala Pro Leu Asp Glu Gln Asn
    50                  55                  60

Ala Lys Arg Trp Tyr Lys Thr Pro Val Lys Ala Gly Asn Leu Ser Val
65                  70                  75                  80

Thr Trp Gln Leu Thr Ala Arg His Lys Thr Ser Thr Trp Asp Tyr Tyr
                85                  90                  95

Ile Thr Lys Pro Ser Trp Asn Pro Asn Ala Pro Leu Lys Phe Ser Asp
            100                 105                 110

Phe Lys Lys Ile Ala Ser Tyr Asn Asp Asn Gly Ala Ile Pro Ser Glu
        115                 120                 125

Phe Val Thr His Gln Val Asn Ile Ser Ala Asn Glu Lys Gly Tyr Gln
    130                 135                 140
```

```
Val Leu Leu Ser Val Trp Asn Ile Ala Asp Thr Gly Asn Ala Phe Tyr
145                 150                 155                 160

Gln Val Ser Asp Ile Asp Val Gln
                165
```

<210> SEQ ID NO 8
<211> LENGTH: 173
<212> TYPE: PRT
<213> ORGANISM: Photorhabdus luminescens

<400> SEQUENCE: 8

```
His Gly Tyr Ile Asp Ser Pro Gly Ser Arg Ala Phe Leu Cys Ser Ala
1               5                   10                  15

Gln Gly Asn Glu Gln Asn Met Asp Cys Gly Leu Val Lys Tyr Glu Pro
            20                  25                  30

Gln Ser Leu Glu Ala Lys Lys Gly Phe Pro Gln Ala Gly Pro Glu Asp
        35                  40                  45

Gly His Ile Ala Ser Ala Gly Ile Gly His Phe Gly Ala Leu Asp Ala
    50                  55                  60

Gln Thr Glu Asp Arg Trp Lys Lys Ile Pro Ile Thr Ala Gly Glu Ile
65                  70                  75                  80

Glu Phe Gln Trp Glu Ile Met Ile Gln His Lys Thr Ser Ser Trp Glu
                85                  90                  95

Tyr Phe Ile Thr Lys Leu Gly Trp Asp Pro Asn Lys Pro Leu Thr Arg
            100                 105                 110

Glu Gln Phe Asn Ser Thr Pro Phe Cys Phe Glu Asp Tyr Gln Glu Lys
        115                 120                 125

Met Pro Ser Ser Arg Val Ile Asn Lys Cys Thr Leu Pro Glu Gly Tyr
    130                 135                 140

Gln Gly Tyr His Val Ile Leu Gly Val Trp Thr Ile Ser Asp Thr Leu
145                 150                 155                 160

Asn Ala Phe Tyr Gln Val Ile Asp Thr Thr Ile Ser Pro
                165                 170
```

<210> SEQ ID NO 9
<211> LENGTH: 180
<212> TYPE: PRT
<213> ORGANISM: Lactococcus lactis

<400> SEQUENCE: 9

```
His Gly Tyr Val Gln Ser Pro Pro Ala Arg Gly Tyr Gln Gly Gln Leu
1               5                   10                  15

Asp Ser Gln Ser Leu Gly Trp Thr Ala Ala Phe Asn Ile Tyr Gly Asn
            20                  25                  30

Val Ile Ser Asn Pro Gln Ser Leu Glu Ala Pro Lys Gly Phe Pro Glu
        35                  40                  45

Cys Gly Pro Ala Asp Gly Arg Ile Ala Ser Ala Asn Gly Gly Leu Gly
    50                  55                  60

Gln Ile Gly Asp Phe Val Leu Asp Asn Gln Thr Ser Ser Arg Trp Lys
65                  70                  75                  80

Lys Thr Ser Ile Ser Thr Gly Ser Asn Ile Phe Thr Trp Lys Tyr Thr
                85                  90                  95

Ala Pro His Lys Thr Thr Lys Trp His Tyr Tyr Met Thr Lys Thr Gly
            100                 105                 110

Trp Asp Gln Asn Ala Pro Leu Lys His Ser Glu Leu Glu Leu Ile Gly
        115                 120                 125

Thr Ile Asn His Asp Gly Ser Pro Ala Thr Asn Asn Leu Ser His Thr
```

```
                130                 135                 140
Ile Asn Ile Pro Thr Asp Arg Ser Gly Tyr His Ile Val Leu Ala Val
145                 150                 155                 160

Trp Asp Val Ala Asp Thr Ser Asn Ala Phe Tyr Asn Val Ile Asp Ile
                165                 170                 175

Asn Val Asn Asn
            180

<210> SEQ ID NO 10
<211> LENGTH: 179
<212> TYPE: PRT
<213> ORGANISM: Bacillus amyloliquefaciens

<400> SEQUENCE: 10

His Gly Tyr Ile Lys Glu Pro Val Ser Arg Ala Tyr Met Gly Ala Leu
1               5                   10                  15

Glu Lys Gln Thr Met Gly Trp Thr Ala Ala Ala Gln Lys Tyr Gly Ser
                20                  25                  30

Val Ile Asp Asn Pro Gln Ser Val Glu Gly Pro Lys Gly Phe Pro Ala
            35                  40                  45

Ala Gly Pro Pro Asp Gly Arg Ile Ala Ser Ala Asn Gly Gly Ser Gly
    50                  55                  60

Gln Ile Asp Phe Gly Leu Asp Lys Gln Thr Ala Asp His Trp Val Lys
65                  70                  75                  80

Gln Asn Ile Arg Gly Gly Phe Asn Thr Phe Thr Trp His Tyr Thr Ala
                85                  90                  95

Pro His Ala Thr Ser Lys Trp His Tyr Tyr Ile Thr Lys Lys Asn Trp
            100                 105                 110

Asn Pro Asn Lys Pro Leu Ser Arg Asp Glu Phe Glu Leu Ile Gly Thr
        115                 120                 125

Val Asn His Asp Gly Ser Lys Ala Asp Thr Asn Leu Thr His Lys Ile
    130                 135                 140

Phe Val Pro Thr Asp Arg Ser Gly Tyr His Ile Ile Leu Gly Val Trp
145                 150                 155                 160

Asp Val Ala Asp Thr Ser Asn Ala Phe Tyr Asn Val Ile Asp Val Asn
                165                 170                 175

Leu Thr Lys

<210> SEQ ID NO 11
<211> LENGTH: 166
<212> TYPE: PRT
<213> ORGANISM: Listeria monocytogenes

<400> SEQUENCE: 11

His Gly Tyr Ile Ser Lys Pro Ala Ser Arg Val Tyr Leu Ala Asn Lys
1               5                   10                  15

Gly Ile Asn Val Gly Val Gly Ser Ala Gln Tyr Glu Pro Gln Ser Val
                20                  25                  30

Glu Ala Pro Lys Gly Phe Pro Ile Ser Gly Pro Ala Asp Gly Ser Ile
            35                  40                  45

Ala Gly Gly Gly Lys Tyr Ser Leu Leu Asp Glu Gln Ser Ala Ser Arg
    50                  55                  60

Trp Ala Lys Val Asp Ile Glu Ser Gly Pro Leu Thr Val Glu Trp Thr
65                  70                  75                  80

Leu Thr Ala Pro His Lys Thr Ser Ser Trp Gln Tyr Phe Ile Thr Lys
                85                  90                  95
```

```
Lys Gly Trp Asp Pro Asn Lys Pro Leu Thr Arg Ser Ser Leu Glu Pro
            100                 105                 110

Leu Ala Thr Ile Glu Ala Asp Gly Ser Val Pro Asn Ala Leu Ala Lys
            115                 120                 125

Gln Glu Ile Asn Ile Pro Asn Asp Arg Ser Gly Tyr Tyr Leu Ile Leu
        130                 135                 140

Gly Val Trp Asn Ile Ala Asp Thr Gly Asn Ala Phe Tyr Gln Val Ile
145                 150                 155                 160

Asp Ala Asn Ile Ile Asn
                165

<210> SEQ ID NO 12
<211> LENGTH: 171
<212> TYPE: PRT
<213> ORGANISM: Streptomyces olivaceoviridis

<400> SEQUENCE: 12

His Gly Tyr Thr Asp Leu Pro Val Ser Arg Gln Lys Met Cys Gln Asn
1               5                   10                  15

Gly Met Val Thr Asn Cys Gly Asn Ile Gln Trp Glu Pro Gln Ser Val
            20                  25                  30

Glu Gly Pro Lys Phe Pro Ser Gly Gly Pro Ala Asp Gly Arg Ile Cys
        35                  40                  45

Ser Ala Gly Asn Thr Ser Phe Ala Gln Leu Asp Ser Pro Arg Thr Pro
    50                  55                  60

Ser Gly Gly Ala Trp Pro Thr Thr Arg Val Thr Gly Gly Gln Asn Tyr
65                  70                  75                  80

Thr Phe Arg Trp Gln Phe Thr Ala Met His Ala Thr Thr Asp Phe Lys
                85                  90                  95

Tyr Tyr Val Thr Lys Pro Gly Trp Asn Gln Asp Arg Ala Leu Thr Arg
            100                 105                 110

Ala Asp Leu Asn Leu Thr Pro Phe Leu Thr Val Pro Tyr Gly Gly Gln
        115                 120                 125

Arg Pro Pro Gln Thr Leu Ser His Ser Gly Gln Leu Pro Ser Gly Leu
    130                 135                 140

Ser Gly His His Val Val Leu Ala Val Trp Thr Val His Asp Thr Gly
145                 150                 155                 160

Asn Ala Phe Tyr Ala Cys Ser Asp Val Thr Phe
                165                 170

<210> SEQ ID NO 13
<211> LENGTH: 170
<212> TYPE: PRT
<213> ORGANISM: Serratia marcescens

<400> SEQUENCE: 13

His Gly Tyr Val Glu Ser Pro Ala Ser Arg Ala Tyr Gln Cys Lys Leu
1               5                   10                  15

Gln Leu Asn Thr Gln Cys Gly Ser Val Gln Tyr Glu Pro Gln Ser Val
            20                  25                  30

Glu Gly Leu Lys Gly Phe Pro Gln Ala Gly Pro Ala Asp Gly His Ile
        35                  40                  45

Ala Ser Ala Asp Lys Ser Thr Phe Phe Glu Leu Asp Gln Gln Thr Pro
    50                  55                  60

Thr Arg Trp Asn Lys Leu Asn Leu Lys Thr Gly Pro Asn Ser Phe Thr
65                  70                  75                  80

Trp Lys Leu Thr Ala Arg His Ser Thr Thr Ser Trp Arg Tyr Phe Ile
```

|  |  |  |  | 85 |  |  |  | 90 |  |  |  | 95 |  |  |
|---|---|---|---|---|---|---|---|---|---|---|---|---|---|---|
| Thr | Lys | Pro | Asn | Trp | Asp | Ala | Ser | Gln | Pro | Leu | Thr | Arg | Ala | Ser | Phe |
|  |  |  | 100 |  |  |  |  | 105 |  |  |  |  | 110 |  |  |
| Asp | Leu | Thr | Pro | Phe | Cys | Gln | Phe | Asn | Asp | Gly | Gly | Ala | Ile | Pro | Ala |
|  |  | 115 |  |  |  |  | 120 |  |  |  |  | 125 |  |  |  |
| Ala | Gln | Val | Thr | His | Gln | Cys | Asn | Ile | Pro | Ala | Asp | Arg | Ser | Gly | Ser |
|  | 130 |  |  |  |  | 135 |  |  |  |  | 140 |  |  |  |  |
| His | Val | Ile | Leu | Ala | Val | Trp | Asp | Ile | Ala | Asp | Thr | Ala | Asn | Ala | Phe |
| 145 |  |  |  | 150 |  |  |  | 155 |  |  |  |  | 160 |  |  |
| Tyr | Gln | Ala | Ile | Asp | Val | Asn | Leu | Ser | Lys |
|  |  |  | 165 |  |  |  |  | 170 |  |